United States Patent
Gu et al.

(10) Patent No.: US 9,782,471 B2
(45) Date of Patent: Oct. 10, 2017

(54) EV71 VIRUS-LIKE PARTICLES AND PREPARATION METHOD AND APPLICATION THEREOF

(71) Applicant: BEIJING MINHAI BIOTECHNOLOGY CO., LTD., Beijing (CN)

(72) Inventors: Meirong Gu, Beijing (CN); Wenjin Wei, Beijing (CN); Jiankai Liu, Beijing (CN); Linlin Song, Beijing (CN); Shanshan Xu, Beijing (CN); Guoshun Li, Beijing (CN); Lin Guo, Beijing (CN)

(73) Assignee: BEIJING MINHAI BIOTECHNOLOGY CO., LTD. (CN)

( * ) Notice: Subject to any disclaimer, the term of this patent is extended or adjusted under 35 U.S.C. 154(b) by 0 days.

(21) Appl. No.: 14/891,582

(22) PCT Filed: Apr. 25, 2014

(86) PCT No.: PCT/CN2014/076240
§ 371 (c)(1),
(2) Date: Nov. 16, 2015

(87) PCT Pub. No.: WO2014/183548
PCT Pub. Date: Nov. 20, 2014

(65) Prior Publication Data
US 2016/0166675 A1    Jun. 16, 2016

(30) Foreign Application Priority Data
May 15, 2013  (CN) .......................... 2013 1 0179673

(51) Int. Cl.
| | |
|---|---|
| *A61K 39/135* | (2006.01) |
| *C07K 14/005* | (2006.01) |
| *C12N 7/00* | (2006.01) |
| *A61K 39/125* | (2006.01) |
| *A61K 39/12* | (2006.01) |
| *A61K 39/00* | (2006.01) |

(52) U.S. Cl.
CPC ............ *A61K 39/135* (2013.01); *A61K 39/12* (2013.01); *A61K 39/125* (2013.01); *C07K 14/005* (2013.01); *C12N 7/00* (2013.01); *A61K 2039/5258* (2013.01); *A61K 2039/55505* (2013.01); *C12N 2770/32323* (2013.01); *C12N 2770/32334* (2013.01); *C12N 2770/32351* (2013.01)

(58) Field of Classification Search
None
See application file for complete search history.

(56) References Cited

U.S. PATENT DOCUMENTS

| | | | | |
|---|---|---|---|---|
| 5,389,525 A | * | 2/1995 | Hollenberg | .......... C07K 14/005 435/254.2 |
| 2011/0262474 A1 | * | 10/2011 | Du | .......... A61K 39/21 424/188.1 |
| 2016/0166675 A1 | * | 6/2016 | Gu | .......... A61K 39/12 424/186.1 |

FOREIGN PATENT DOCUMENTS

| | | |
|---|---|---|
| CN | 101831410 A | 9/2010 |
| CN | 102559615 A | 7/2012 |
| CN | 102925476 A | 2/2013 |

OTHER PUBLICATIONS

Chung et al. (Vaccine. 2010; 28: 6951-6957).*
Wang and Yu (Journal of Biomedical Science. 2014; 21 (1): 31).*
Abzug (Journal of Infection; 2014; 68: S108-S114).*
Sequence alignment of Seq ID No. 1 with geneseq database access No. AYK33280 by Zeng et al. in CN101831410 on Sep. 2010.*
Sequence alignment of Seq ID No. 3 with geneseq database access No. AYK33281 by Zeng et al. in CN101831410 on Sep. 2010.*
Valdes-Hevia et al. (FEBS. 1989; 258 (2): 313-316).*
International Search Report for International Application No. PCT/CN2014/076240, dated Aug. 13, 2014 (2 pages).

* cited by examiner

*Primary Examiner* — Shanon A Foley
(74) *Attorney, Agent, or Firm* — Brinks Gilson & Lione; Ryan L. Marshall; Jonathan Hartley

(57) ABSTRACT

The present invention provides EV71 virus-like particles and a preparation method and application thereof. The method comprises: connecting a P1 protein gene and a 3CD protease gene of an EV71 virus with a PMV plasmid to construct a PMV-P1-3CD recombinant expression plasmid; then transforming a *Hansenula polymorpha* AU-0501 expression strain with the PMV-P1-3CD recombinant expression plasmid to obtain an AU-PMV-P1-3CD recombinant expression strain; fermenting and culturing the recombinant expression strain, and inducing the recombinant expression strain to express the EV71 virus-like particle protein with methanol; centrifuging and collecting mycelia for homogeneous breakage at a high pressure; and purifying the supernatant through ion-exchange chromatography, hydrophobic chromatography, and molecular sieve chromatography, so as to obtain EV71 virus-like particles.

14 Claims, 6 Drawing Sheets

Construction of the recombinant expression vector PMV-P1:

Figure 12a

Construction of the recombinant expression vector PMV-3CD:

EV71 VIRUS-LIKE PARTICLES AND PREPARATION METHOD AND APPLICATION THEREOF

RELATED APPLICATIONS

This application is a 371 national phase of International Application No. PCT/CN2014/076240, filed Apr. 25, 2014, designating the United States, which claims the benefit of priority to Chinese Patent Application No. 201310179673.3, filed May 15, 2013, the entire contents of each of which are incorporated herein by reference.

TECHNICAL FIELD

The present invention relates to the field of biotechnology, specifically, to enterovirus 71 virus-like particles and a preparation method thereof, as well as a hand, foot and mouth disease vaccine prepared therefrom.

BACKGROUND

Hand, foot and mouth disease (HFMD) is one of the common infectious diseases caused by enterovirus. The highest morbidity is found in infants under 5 years old. In every year, June to August is the epidemic season, and the main routes of transmission are through the respiratory tract and oral infection. HFMD has characteristics of strong infection, wide route of transmission, rapid transmission, big epidemic intensity, and it can cause pandemics in a short period of time. Enterovirus 71 (EV71) and coxsackievirus A16 (CA16) are the main pathogens of HFMD. As compared with CA16, EV71 is much more dangerous, and more than 90% of severe cases and death cases are caused by EV71 virus. EV71 can invade the vital organs such as heart, brain, and kidney, resulting in serious complications, such as acute flaccid paralysis, encephalitis, aseptic meningitis, myocarditis, hepatitis, neonatal septicemia, and the like, which pose a serious threat to the physical and mental health of children. In recent years, the incidence of hand, foot and mouth disease persists to ascending in China. A data published by the Ministry of Health shows that a total of more than 2,198,000 incident cases of HFMD with 569 deaths are reported in China in 2012, and there is an increase in both the morbidity and mortality as compared with the data in 2011. Viewed from recent years' situation, the number of patient in China increases each year, grows fast, has a wide distribution, and most of the patients are in undeveloped areas, which bring huge loss to the country and also affect the social security. HFMD has become a focus of the party and the government as well as the people of concern.

At present, there are neither vaccines in the market useful for preventing HFMD, nor drugs effective in treating infected patients in the world. Although there are international reports on the research progress of subunit vaccines, DNA vaccines and attenuated live vaccines, none of them can achieve a satisfactory effect on animal protection. Some attenuated live vaccines have risk of reverting to virulence and they can also cause mild neurologic clinical symptoms, and thus the safety of a vaccine remains uncertain. It is currently known that all EV71 vaccines declared to the State Food and Drug Administration are all inactivated vaccines, and such vaccines have some disadvantages such as certain destroyed antigen targeted, poor immunogenicity and excessive dosage, and the doubtful applicability of currently used animal model. Experiments in vitro show that the inactivated EV71 whole virus vaccine has no neutralizing effect on many EV71 strains isolated from the clinical samples; further, it has no protection effect in the infected immature rat model; and the inactivated vaccine has risk of being inactivated incompletely. Therefore, development of a prophylactic EV71 vaccine with high cost-effectiveness is of important significance for preventing HFMD infected with EV71.

The emergence of Virus-like Particle (VLP) vaccine provides a new opportunity to develop a novel, safe and efficient vaccine. VLP vaccine expresses one or more structural proteins of a virus by molecular biotechnology. These structural proteins have an ability of native self assembly, and they can form a steric configuration and an antigenic epitope similar to those of the naturally occurring virus particle, but they do not carry a viral nucleic acid, have strong immunogenicity, and have no infectivity, and thus have no risk of inactivated incompleteness or reverting to virulence. Meanwhile, there are virus antigens with high density on the surface of vaccines which retain the conformational epitopes, and the VLP vaccine can be delivered to immune cells through the same route as the whole virus vaccine to effectively induce the body immune system, in order to produce a protective immune response. In this regard, the VLP vaccine is also superior to the inactivated vaccine in which some important antigenic determinants may be destroyed during inactivation. In addition, another advantage of the VLP vaccine is that it can be engineered arbitrarily as required so as to make it better stimulate the body immune system to produce a protective immune response.

EV71 are small RNA virus, viral genome of EV71 is a single stranded RNA of about 7.4 kb. The virus particle is an icosahedron sphere structure that is three-dimensionally symmetric, without envelope and protrusion, and has a diameter of about 24-30 nm. The capsid of the virus particle consists of 60 subunits, and each subunit has a pentamer-like structure which is assembled by 4 capsid proteins (VP1-VP4). Studies show that four structural proteins of EV71 can self assemble into a structure of VLP in cells, which has a spatial structure similar to the naturally occurring virus. Currently, many research institutions at home and broad are all developing EV71 virus-like particle (EV71 VLP) vaccines. The assembly of EV71 is carried out by co-expression of viral protease 3CD and P1 precursor protein, the process of P1 precursor protein by 3CD protease to produce 4 structural proteins, and the self assembly of 4 structural proteins into a VLP, which does not carry viral nucleic acid, has no potential risk of getting cancer, and has good safety, immunological property and biological activity, furthermore, it can be prepared and purified in a large scale. Thus, VLP vaccines have been a main direction for developing prophylactic EV71 vaccines.

A key to develop EV71 VLP prophylactic vaccines is that VLP samples can be prepared efficiently in a large scale, and the prokaryotic expression system and the eukaryotic expression system are currently the most commonly used expression system.

Most proteins expressed in the prokaryotic expression system lose their natural conformation, and thus they cannot produce protective antibodies. On the other hand, most expression products may be inclusion bodies. The inclusion bodies have complex denaturation and renaturation steps, big loss of proteins, and low yield, such that it is difficult to achieve the large scale production. There are also examples of soluble expression, but the expression level is low and it is difficult to purify the proteins of interest. It is also reported that fusion and expression are performed to increase the solubility and expression level of the interest proteins, although it is relatively easy to perform purification, the cleavage of fusion proteins needs expensive enzymes, such that large scale production cannot be achieved.

The commonly used eukaryotic expression systems include mammalian cell expression system, insect baculovirus expression system and yeast expression systems. Proteins can spontaneously form VLP in the eukaryotic expression system, providing a great convenience for the purification process. However, since VLP is prepared mainly using insect cells, it needs a high cultural condition and has complicated purification process, thereby limiting the need for large scale production; furthermore, baculovirus-insect cell expression system produces baculovirus particles and other pollutants that significantly influence the effect of vaccine, it is very difficult to separate baculoviruses from the prepared VLP, and the measures such as inactivated treatment are required, which have great effect on the quality of vaccines. The mammalian cell expression system plays a role in the process, modification and correct fold of the protein after expression, but it is difficult to artificially control the mammalian cell expression system and the cost for the control is high, and thus the application of the mammalian cell expression system is limited. *Hansenula polymorpha* expression system not only has characteristics of stable heredity, simple operation, being easy to high density culture, high production levels of foreign proteins, low production cost, being suitable for industrial production, and the like, but also has advantages of foreign protein post-translation processing which is not found in the prokaryotic expression system, and meanwhile avoiding the disadvantages of unstable expression strains, easy to lose plasmid, hyperglycosylation etc. present in the other yeasts. It is a relatively advanced VLP vaccine expression system better than *Escherichia coli* and the other eukaryotic expression systems.

BRIEF SUMMARY

An object of the present invention is to provide EV71 VLPs obtained from the *Hansenula polymorpha* expression system.

Another object of the present invention is to provide an EV71 vaccine.

Further object of the present invention is to provide an expression vector comprising both P1 gene and 3CD gene of EV71 virus.

In order to increase the expression level of a protein, the nucleic acid sequences of the P1 gene and 3CD gene are codon-optimized with the *Hansenula polymorpha* biased codons in the present invention. The nucleotide sequences of genes P1 and 3CD provided in the present invention were deleted the sequences encoding the secretion signal peptide and the transcription termination signal recognized by the yeast. Codons of genes encoding the P1 and 3CD proteins in the present invention are the codons most biased by *Hansenula polymorpha*. The codon usage frequency of *Hansenula polymorpha* may refer to kazusa.or.jp/codon/. In order to avoid the translated mRNA having higher content of GC, and the secondary structure of mRNA affecting the efficiency of translation, secondary biased codons are used in the present invention, provided that the usage frequency of the secondary biased codon is very close to that of the most biased codon and the original amino acid sequence remains unchanged. In certain cases, sequences at certain positions are performed appropriate adjustment in order to decrease or increase the enzyme digested sites. Polynucleotides of P1 and 3CD proteins of the EV71 is optimally synthesized using *Hansenula polymorpha* codons, the amino acid sequence of the P1 protein is shown in SEQ ID NO. 2, and the encoding gene of which is shown in SEQ ID NO. 1; and the amino acid sequence of the 3CD protein is shown in SEQ ID NO. 4, and the encoding gene of which is shown in SEQ ID NO. 3.

In one embodiment of the present invention, the primer sequences of P1 gene for PCR amplification are: F-AGTTTTTGCCCTACTTGATCACAG (SEQ ID NO: 15), R-C GGAATTCTTATTACTGGGTCACGGCCTGTC (SEQ ID NO: 16); and the primer sequences of 3CD gene for PCR amplification are: F-AACCACACCCACCACGTG-TACAGAAAC (SEQ ID NO: 17), R-ACTCGCTATTTCA-GCTTTTCATCTC (SEQ ID NO: 18).

In the recombinant expression vector according to the present invention, the nucleotide sequence of P1 gene of the EV71 virus is:
a) nucleotide sequence as shown in SEQ ID No. 1 in the Sequence Listing; or
b) nucleotide sequence encoding P1 protein obtained by substituting one or more nucleotides of the nucleotide sequence as shown in SEQ ID No. 1.

The nucleotide sequence of 3CD gene of the EV71 virus is:
a) nucleotide sequence as shown in SEQ ID No. 3 in the Sequence Listing; or
b) Nucleotide sequence encoding 3CD protein obtained by substituting one or more nucleotides of the nucleotide sequence as shown in SEQ ID No. 3.

Wherein, the above recombinant expression vector comprises a methanol oxidase promoter (MOX) or a formate dehydrogenase (FMD) promoter.

Preferably, the above vector comprises a methanol oxidase (MOX) promoter.

Further preferably, the above recombinant expression vector is PMV-P1-3CD.

The present invention further provides a method for preparing the recombinant expression vector PMV-P1-3CD, comprising the following steps:
(1) optimal synthesis of a protein gene: optimally synthesizing the polynucleotides of P1 and 3CD proteins of the EV71 using *Hansenula polymorpha* codons, the amino acid sequence of the P1 protein is shown in SEQ ID NO. 2, and the encoding gene of which is shown in SEQ ID NO. 1; the amino acid sequence of the 3CD protein is shown in SEQ ID NO. 4, and the encoding gene of which is shown in SEQ ID NO. 3;
(2) Construction of recombinant expression vector: connecting P1 protein gene and 3CD protease gene of the EV71 with a PMV plasmid to obtain PMV-P1-3CD recombinant expression plasmid;

Further, the present invention provides a host cell containing the above recombinant expression vector.

Still further, the host cell is a *Hansenula polymorpha* cell.

The *Hansenula polymorpha* cells are ATCC34438 and ATCC26012.

Preferably, the *Hansenula polymorpha* cell is ATCC26012 uracil defective host cell. The ATCC26012 uracil defective host cell used in the present invention is *Hansenula polymorpha* AU-0501, which has been deposited in China General Microbiological Culture Collection Center (Address: Datun Road, Chaoyang District, Beijing, China, Institute of Microbiology, Chinese Academy of Science, CGMCC for short, Postcode: 100101) on Dec. 18, 2012, with an Accession No. of CGMCC No. 7013, and a classification name of *Hansenula polymorpha*.

Further, a *Hansenula polymorpha* AU-0501 cell is transformed with the recombinant expression vector to obtain an AU-PMV-P1-3CD recombinant expression strain.

In one embodiment of the present invention, the *Hansenula polymorpha* host bacteria is transformed electrically with the PMV-P1-3CD recombinant expression plasmid, and the recombinant expression strains are screened through the selective medium; the recombinant expression strain is fermented and cultured, and inducible expression of EV71 VLP protein is performed by using methanol.

Therefore, the present invention provides use of the recombinant expression vector in the preparation of EV71 viral vaccines.

The present invention successfully obtains EV71 VLPs by constructing and culturing a *Hansenula polymorpha* recombinant expression strain which can express EV71 VLPs, and which are easy to be cultured by the way of fermentation, suitable for industrializing production, and easy to be purified. The EV71 VLPs are prepared by the steps of: (1) transforming a *Hansenula polymorpha* AU-0501 expression strain with the recombinant expression vector according to the present invention to obtain an AU-PMV-P1-3CD recombinant expression strain; (2) fermenting and culturing the recombinant expression strain; (3) isolation and purification of the EV71 VLPs, comprising centrifuging and collecting mycelia for homogeneous breakage at a high pressure, clarifying, ultrafiltering, and precipitating the virus particles, ultracentrifuging and collecting the supernatant, purifying the supernatant through ion-exchange chromatography, hydrophobic chromatography or molecular sieve chromatography, so as to obtain the EV71 VLPs.

In the method for preparing the EV71 VLPs, the breakage includes resuspending the *Hansenula polymorpha* cells obtained by fermenting the AU-PMV-P1-3CD recombinant expression strains in the cell lysis buffer (20 mmol/L $NaH_2PO_4$, 2 mmol/L EDTA-$Na_2$, 0.4 mol/L NaCl, pH 7.5) for washing twice, and then resuspending the cells in the cell lysis buffer containing 2 mmol/L PMSF, 1% Tween-20, 3% PEG 6000 in a ratio of 1:4 (w/v), and breaking cells twice at the operation pressure of 1100 bar with a high pressure homogenizer, so as to make the cell broken rate reach more than 95%.

In the method described above, the clarifying comprises pouring the broken cell lysate into the centrifuge bowl, centrifuging for 20 min at 8000 rpm, collecting the supernatant and microfiltering with a 0.45 μm membrane to remove the macromolecular substances.

In the method described above, the ultrafiltering comprises ultrafiltering the clarified protein solution with a 50 KD membrane to remove the small molecular substances.

The precipitating the virus particle comprises adjusting the ultrafiltered protein solution with 0.5M NaOH to pH6.5, adding 5M NaCl solution, adding 0.5 g/ml PEG 6000 solution in drop-wise under stirring condition to a final concentration of 0.12 g/ml, standing for 2 h at 4° C., centrifuging at 12000 rpm for 30 min at 4° C., discarding the supernatant, and dissolving the precipitate with an appropriate volume of 20 mmol/L PB and re-centrifuging at 5000 rpm for 30 min at 4° C., and collecting the supernatant centrifuged in the second time to obtain the crude pure protein solution.

The ultracentrifugation comprises adding potassium bromide solid into the crude pure protein solution to adjust the density to 1.25 g/ml. The order for loading samples of ultracentrifugation is: 150 ml of NaCl-EDTA; 300 ml of 1.25 KBr sample solution; 700 ml of 1.30 KBr gradient solution; and 540 ml of 1.35 KBr gradient solution. The ultracentrifugation is performed at 25000 rpm for 4 h at 8° C., the solutions having ultraviolet absorption peaks at UV 280 nm are collected in individual tubes using 1.35 KBr solution as the upper solution, samples are taken from the solution in each tube for detection by SDS-PAGE, and the results are shown in FIG. 10.

Molecular sieve chromatography: taking Sephacryl S-500HR as an example, elution is carried out in PBS (pH7.0), the eluent having ultraviolet absorption peaks at UV 280 nm are collected to obtain the purified protein solution.

Determination of the concentration of purified proteins (Lowry method): 0 ml, 0.2 ml, 0.4 ml, 0.6 ml, 0.8 ml, 1.0 ml of the standard protein, viz. bovine serum albumin solution (100 μg/ml) are accurately weighted, placed in test tubes respectively, adding distilled water is added therein to 1 ml, and meanwhile 1 ml of purified protein solution in 4 times of dilution are weighted and placed in the test tubes, 5 ml alkaline copper solution and 0.5 ml phenol reagent are added into the test tubes respectively, and the absorbance value at 650 nm of wave length in colorimetric cuvette is determined. The standard curve is plotted using the protein content of the standard protein as abscissa and the absorbance value as coordinate. In one embodiment of the present invention, the purified protein has a final concentration of 207 μg/ml, as determined by Lowry method.

The present invention also provides a hand, foot and mouth disease vaccine comprising the EV71 VLPs.

The present invention also provides a method for preparing the hand, foot and mouth disease vaccine, comprising absorbing the EV71 VLP with an aluminum phosphate adjuvant to prepare a vaccine comprising 20 μg/ml VLPs.

Specifically, the present invention provides a method for preparing the hand, foot and mouth disease vaccine, comprising: (1) optimal synthesis of protein genes, comprising optimally synthesizing the polynucleotides of P1 and 3CD proteins of the EV71 using *Hansenula polymorpha* codons, the amino acid sequence of the P1 protein is shown in SEQ ID NO. 2, and the encoding gene of P1 protein is shown in SEQ ID NO. 1; the amino acid sequence of the 3CD protein is shown is SEQ ID NO. 4, and the encoding genes of 3CD protein is shown in SEQ ID NO. 3; (2) construction of a recombinant expression vector, comprising connecting P1 protein gene and 3CD protease gene of the EV71 with a PMV plasmid to construct a PMV-P1-3CD recombinant expression plasmid; (3) transformation of the expression strains with the recombinant expression plasmid, comprising transforming a *Hansenula polymorpha* AU-0501 expression strain with the recombinant expression plasmid to obtain an AU-PMV-P1-3CD recombinant expression strain; (4) fermentation culture of the recombinant expression strains and purification of the EV71 VLPs, comprising culturing the above expression strains in a 30 L fermentation tank, centrifuging and collecting the mycelia to perform homogenate crushing at a high pressure, centrifuging and collecting the supernatant, purifying the above supernatant through microfiltration, ultrafiltration, PEG precipitation, ultracentrifugation, molecular sieve chromatography and the like to obtain the EV71 VLPs; (5) preparation of a vaccine, comprising absorbing the EV71 VLPs with an aluminum phosphate adjuvant to prepare a vaccine comprising 20 μg/ml VLPs.

The beneficial effects of the present invention lie in that:

(1) it is easy to obtain high level expression strains. The present invention optimally designs gene sequences of the P1 and 3CD proteins of EV71, and provides a recombinant expression vector which expresses EV71 VLPs in high level, and achieves high level expression of VLP$_S$ by *Hansenula polymorpha* expression system;

(2) the present application is suitable for industrial production. *Hansenula polymorpha* recombinant expression strains screened in the present invention are characterized by fast growth of the prokaryotic cells, simple genetic manipulation, easy culture, low production cost, ability to accommodate high density fermentation culture, and high production levels of foreign proteins, and applicability for large scale production etc;

(3) the plasmids according to the present application have good stability. The recombinant expression plasmids can perform homologous recombination with the chromosomal genome DNA in the yeast host cells, and the resultant plasmids have good stability and are not easily lost; the products expressed by fermentation are stored in the peroxysome, which protect them from degradation by protease;

(4) The EV71 VLPs in the present invention are suitable for preparing vaccines. The proteins according to the present invention can be processed, modified and folded correctly without hyperglycosylation. After purification of the products expressed by fermentation, the purified samples under electro-microscope exhibit VLPs with a particle size of around 30 nm, and the particle is integral and regular. The EV71 VLPs according to the present invention do not carry viral nucleic acids, have no potential cancerogenic risk, and have good safety, immunological property and biological activity, and they may be prepared and purified in a large scale and may be used for preparing VLP vaccines, and thus have good economic value and application prospect.

BRIEF DESCRIPTION OF THE DRAWINGS

FIG. 1 shows the PCR detection of *E. coli* transformed clones of the recombinant expression plasmid PMV-P1 and PMV-3CD.

FIG. 4 is detection result of *E. coli* transformed clones of the recombinant expression plasmid PMV-P1-3CD identified by PCR; wherein, in FIG. 4a, 1-12 are results of identification of P1 gene identified by PCR (size: 1000 bp); in FIG. 4b, 13-24 are result of identification of 3CD gene by PCR (size: 630 bp); M: DL2000 (Takara Biotechnology Co., Ltd.).

FIG. 12 is a schematic diagram of construction of the recombinant expression plasmid, wherein FIG. 12a is a schematic diagram of construction of PMV-P1, and FIG. 12b is a schematic diagram of construction of PMV-3CD expression vector.

FIG. 13 is a schematic diagram of construction of the recombinant expression plasmid PMV-P1-3CD.

DETAILED DESCRIPTION OF THE INVENTION

Figure 1A:
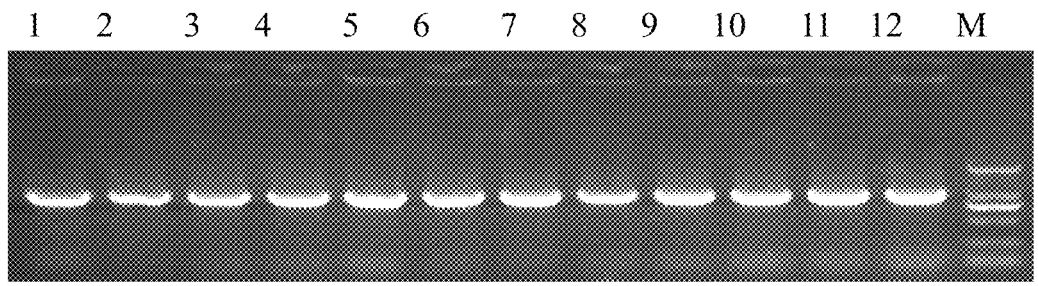
FIG. 1a, the gel results of P1.

The following Examples are used for illustrating the present invention, but not for limiting the scope of the present invention. Unless otherwise indicated, all Examples are carried out according to the conventional experiment conditions, such as Sambrook J & Russell D W, Molecular cloning: a laboratory manual, 2001, or according to the conditions recommended by the manufacturer's instructions.

Example 1

Optimization of Gene Sequences Encoding P1 and 3CD Proteins of EV71

According to the nucleotide sequences of P1 and 3CD proteins of C4a subtype of EV71 epidemic in China, the gene sequences of P1 and 3CD proteins were optimized with the most biased codons of *Hansenula polymorpha* using vector software to increase the expression level of the P1 and 3CD genes in *Hansenula polymorpha* cells. The nucleotide sequences of genes encoding P1 and 3CD proteins provided in the present invention were deleted the sequences encoding the secretion signal peptide and the transcription termination signal recognized by the yeast. Codons of genes encoding the P1 and 3CD proteins used in the present invention are the most biased codons of *Hansenula polymorpha*. For the codon usage frequency of *Hansenula polymorpha* (*Pichia angusta*), please refer to kazusa.or.jp/codon/. In order to avoid the translated mRNA having higher content of GC and the secondary structure of mRNA affecting the efficiency of translation, secondary biased codons are used for some amino acids in the present invention, provided that the usage frequency of the secondary biased codon is very close to that of the most biased codon, and the order of the original amino acid sequence remained unchanged. In certain very special cases, the order of the sequences at certain positions may be appropriately adjust in order to decrease or increase the enzyme digested sites. Therefore, the present invention optimally designed a P1 gene, the sequence of P1 gene is shown in SEQ ID NO. 1 and the gene P1 sequence is synthesized by Shanghai Generay Biotech Co., Ltd and cloned onto the Dev-C vector (purchased from Shanghai Generay Biotech Co., Ltd), and the amino acid sequence of the P1 protein is shown in SEQ ID NO. 2; 3CD gene was optimally designed in the present invention, the sequence of 3CD gene is shown in SEQ ID NO. 3 and the gene 3CD sequence is synthesized by Shanghai Generay Biotech Co., Ltd, and cloned onto the Dev-C vector (purchased from Shanghai Generay Biotech Co., Ltd). The amino acid sequence of the 3CD protein is shown in SEQ ID NO. 4.

Example 2

Construction of the Recombinant Expression Vector PMV-P1-3CD

1. Construction of Expression Vector PMV-05:

The expression vector PMV-05 of the present invention consists of 6 parts: promoter (MOX-P), terminator (MOX-T), replicon HARS, ura3 gene, ColE1 replicon, and Amp resistance gene.

In order to obtain the genes MOXP, MOXT, HARS and Ura3, PCR amplification was performed using a yeast genomic DNA as a template and using MOXP-F (sequence shown in SEQ ID NO. 5), MOXP-R (shown in SEQ ID NO. 6); MOXT-F (shown in SEQ ID NO. 7), MOXT-R (shown in SEQ ID NO. 8); HARS-F (shown in SEQ ID NO. 9), HARS-R (shown in SEQ ID NO. 10); Ura3-F (shown in SEQ ID NO. 11) and Ura3-R (shown in SEQ ID NO. 12) as primers respectively. In order to obtain the gene Amp+ColE1, PCR amplification was performed using a PBR-SK plasmid (purchased from Takara Biotechnology (Dalian) Co., Ltd., Article No.: D3050) as a template and using primers Amp+ColE1-F (as shown in SEQ ID NO. 13), Amp+ColE1-R (as shown in SEQ ID NO. 14). PCR reaction system was as follows: 10 μl of PCR buffer, 10 μl of dNTP, 1 μl of primer F, 1 μl of primer R, 1 μl of Taq DNA polymerase, 157 μl of distilled water, 200 μl of total volume. Reaction conditions were as follows: 95° C. for 2 min; 95° C. for 30 s, 55° C. for 30 s, 72° C. for 2 min; performing 30 cycles. The PCR amplified DNA fragments were detected by 1% agarose gel electrophoresis, the sizes of PCR products were as follows: MOXP: around 1500 bp, MOXT: around 300 bp, HARS: around 500 bp, Ura3: around 1100 bp, Amp+ColE1: around 2200 bp respectively. The above 5 gene fragments were purified with DNA fragment purification kit. PCR amplification was performed using 1 μl of each of the purified MOXP, MOXT gene fragments respectively as templates, and using MOXP-F and MOXT-R as primers to obtain MOXP+MOXT gene fragments, and the reaction system and reaction conditions were the same as above. PCR amplification was performed using 1 μl of each of the purified HARS, Ura3, Amp+ColE1 gene fragments respectively as templates and using HARS-R and Amp+ColE1-R as primers to obtain HARS+Ura3+Amp+ColE1 gene fragments, PCR reaction system was as follows: 10 μl of PCR buffer, 10 μl of dNTP, 1 μl of primer F, 1 μl of primer R, 1 μl of Taq DNA polymerase, 155 μl of distilled water, 200 μl of total volume. Reaction conditions were as follows: 95° C. for 2 min; 95° C. for 30 s, 55° C. for 30 s, 72° C. for 4 min; performing 30 cycles. The gene fragments MOXP+MOXT, HARS+Ura3+Amp+ColE1 were purified with a DNA fragment purification kit. The purified gene fragments MOXP+MOXT and HARS+Ura3+Amp+ColE1 were digested with double enzymes (SacI, SalI) respectively, and the digestion reaction was as follows: 60 μl of gene fragment, 3 μl of each of SacI and SalI, 10 μl of 10×Basal butter, 10 μl of 10×BSA, adding water to 100 μl. The enzyme digestion was performed at 37° C. overnight. The product obtained by the enzyme digestion was separated by agarose gel electrophoresis, and then gene fragments produced by the enzyme digestion were recovered by excising the gel, and ligated using solution I ligation kit (purchased from Takara Biotechnology (Dalian) Co., Ltd.). The ligation reaction system was as follows: 1 μl (SacI, SalI) double enzyme digested and purified products of HARS+Ura3+Amp+ColE1, 4 μl (SacI, SalI) double enzymes digested and purified products of MOXP+MOXT, 5 μl of solution I, a total 10 μl of reaction system, and the ligation reaction was performed for 1 hour at 16° C. The ligated recombinant expression vectors were transformed into a 100 μl of *E. coli* (DH5α) competent cells, plated on LB+Amp (100 μg/ml) solid medium, and cultured in an incubator at 37° C. overnight.

Screen of transformed clones: in order to identify transformed clones, PCR was performed by picking a monoclonal colony on a LB+Amp solid medium as a template and using MOXP-F, MOXP-R, Ura3-F, Ura3-R as primers respectively, the PCR reaction system was as follows: 2 μl of PCR buffer, 2 μl of dNTP, 0.1 μl of primer F, 0.1 μl of primer R, 0.1 μl of Taq DNA polymerase, 15.7 μl of distilled water, and a total volume of 20 μl. Reaction conditions were as follows: 95° C. for 2 min; 95° C. for 30 s, 55° C. for 30 s, 72° C. for 1 min; and performing 30 cycles. The PCR amplified DNA fragments were detected by 1% agarose gel electrophoresis, and the size of the PCR product should be around 1500 bp for MOXP-F and MOXP-R as primers, and around 1000 bp for Ura3-F and Ura3-R as primers. The correct transformed clone 5 identified by PCR was named as recombinant expression plasmid PMV-05, inoculated in 10 ml LB+Amp liquid medium, and cultured at 37° C. in a shaker at 200 rpm overnight. The recombinant expression plasmid PMV-05 was extracted according to the instructions of the plasmid extraction kit (from Beijing TransGen Biotech Co., Ltd.), and the extracted recombinant expression vector was detected by 1% agarose electrophoresis. The obtained expression vector was identified by enzyme digestion. The enzyme digestion reaction volume was as follows: 5 μl of plasmid, 1 μl of each of SacI and SalI, 2 μl of 10×Basal buffer and 2 μl of 10×BSA buffer and adding water to 20 μl. The enzyme digestion was performed for 4 hours at 37° C. The results show that the recombinant expression vector PMV-05 was constructed successfully.

2. Construction of Recombinant Expression Vectors PMV-P1 and PMV-3CD

The genes P1 and 3CD which were synthesized optimally in Example 1 were cloned into a Dev-C vector. EcoRI and BamHI digestion sites were added to both ends of the gene sequence while optimally synthesizing the genes P1 and 3CD, so that the genes can be cloned into an expression vector.

Dev-C vector and the expression vector (PMV-05) into which P1 and 3CD genes have been cloned were subjected to double enzyme digestion with EcoRI and BamHI (both were purchased from Takara Biotechnology (Dalian) Co., Ltd.). The enzyme digestion reaction system was as follows: 30 µl of plasmid, 3 µl of each of EcoRI and BamHI, 10 µl of 10×K buffer buffer and adding water to 100 µl. The enzyme digestion was performed at 37° C. overnight. After isolation by agarose gel electrophoresis, the product obtained by the enzyme digestion, the gene fragment and linear expression vector were recovered by excising the gel, and ligated via Solution I ligation kit (purchased from Takara Biotechnology (Dalian) Co., Ltd.). The ligation reaction system was as follows: 1 µl of double enzyme digested and purified product of the vector PMV-05 (EcoRI/BamHI), 5 µl of double enzyme digested and purified products of each of P1 and 3CD genes (EcoRI/BamHI), 6 µl of Solution I and a total 12 µl of reaction system. The ligation reaction was performed for 1 hour at 16° C. The ligated recombinant expression vectors were transformed into 100 µl of E. coli (DH5α) competent cells, plated on LB+Amp (100 µg/ml) solid medium and cultured in an incubator at 37° C. overnight.

Figure 1B:
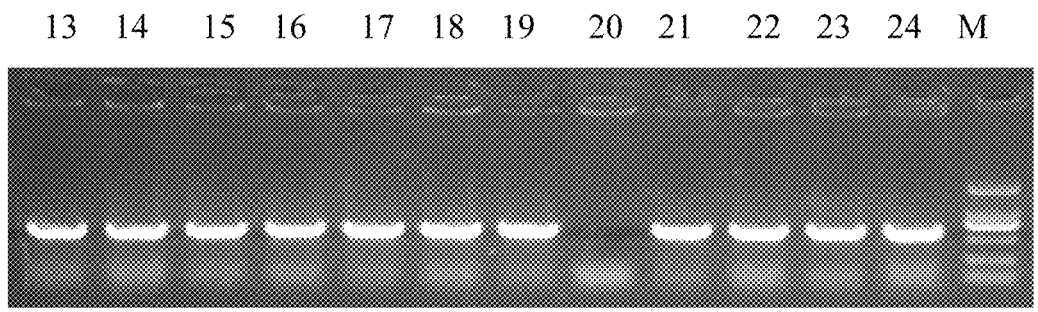
FIG. 1b, the results of 3CD (630 bp); M: marker.
Figure 2:
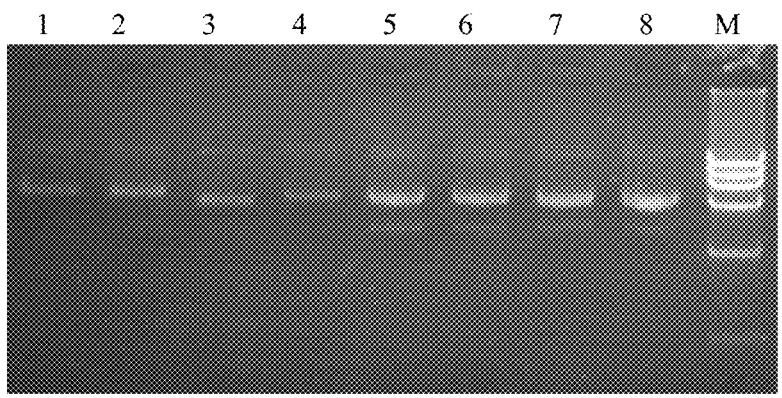
FIG. 2 is the result of detection of the extracted recombinant expression plasmids PMV-P1 and PMV-3CD: wherein 1-2 are the recombinant expression plasmid PMV-P1; 3-8 are the recombinant expression plasmid PMV-3CD; M: DL10000 Plus (Beijing TransGen Biotech Co., Ltd.).
Figure 3:
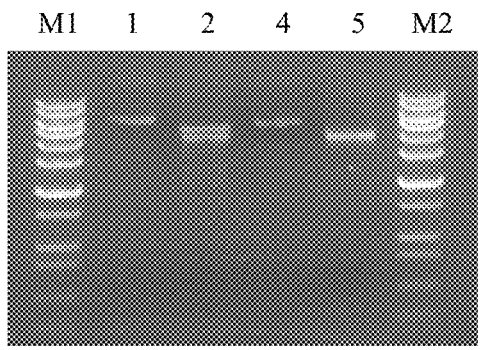
FIG. 3 is results of identification of recombinant expression plasmids PMV-P1 and PMV-3CD by double enzyme digestion with SalI and SacI; wherein 1 is a control for plasmid PMV-P1, 2 is double enzyme digestion of the plasmid PMV-P1 (sizes of the two bands are 4.4 kb and 3.9 kb respectively); 3 is double enzyme digestion of plasmid PMV-3CD (sizes of the two bands are 3.8 kb and 3.9 kb respectively); M: DL10000 Plus (Beijing TransGen Biotech Co., Ltd.).

Screen of transformed clones: the transformed clones were identified by PCR by picking a monoclonal colony on a LB+Amp solid medium as a template. The primer sequences of P1 gene were as follows: primer SEQ ID NO. 15, and primer SEQ ID NO. 16; the primer sequences of 3CD gene were as follows: primer SEQ ID NO. 17, and primer SEQ ID NO. 18 PCR reaction system was as follows: 2 µl of PCR buffer, 2 µl of dNTP, 0.1 µl of primer F, 0.1 µl of primer R, 0.1 µl of Taq DNA polymerase, 15.7 µl of distilled water, and a total volume of 20 µl. Reaction conditions were as follows: 95° C. for 2 min; 95° C. for 30s, 55° C. for 30s, 72° C. for 1 min; performing 30 cycles. The PCR amplified DNA fragments were detected by 1% agarose gel electrophoresis, and the size of the PCR product of P1 gene was about 1000 bp, and the size of the PCR product of 3CD gene was about 630 bp. Results of PCR electrophoresis are shown in Figure 1a and FIG. 1b. The correct transformed clones identified by PCR were named as recombinant expression plasmid PMV-P1 and recombinant expression plasmid PMV-3CD, and schematic diagrams of the construction of the recombinant expression vectors were shown in FIG. 12a and FIG. 12b. The identified correct clones were inoculated in 10 ml LB+Amp liquid medium, and cultured at 37° C. in a shaker at 200rpm overnight. The recombinant expression plasmid PMV-P1 and PMV-3CD were extracted according to the instructions of the plasmid extraction kit (from Beijing TransGen Biotech Co., Ltd.), and the extracted recombinant expression vector were detected by 1% agarose electrophoresis, and the results were shown in FIG. 2. The obtained expression vectors were identified by the enzyme digestion. The enzyme digestion reaction system was as follows: 5 µl of plasmid, 1 µl of each of SacI and SalI, 2 µl of 10×K buffer and adding water to 20 µl. The enzyme digestion was performed for 4 hours at 37° C. The results of electrophoresis detection for enzyme digestion were shown in FIG. 3.

3. Construction of Recombinant Expression Vector PMV-P1-3CD

The recombinant expression vector PMV-P1 was digested with double enzymes SacI and XhoI (both are purchased from Takara Biotechnology (Dalian) Co., Ltd.) and the recombinant expression vector PMV-3CD was digested with double enzymes SacI and SalI (both are purchased from Takara Biotechnology (Dalian) Co., Ltd.). The enzyme digestion reaction volume was as follows: 50 µl of plasmid, 5 µl of each of SalI/XhoI and SacI, 10 µl of 10×K buffer and adding water to 100 µl. The enzyme digestion was performed at 37° C. overnight. After isolation by agarose gel electrophoresis, the products obtained by the enzyme digestion, 3CD gene fragment and PMV-P1 linear vector fragment were recovered by excising the gel, and ligated via Solution I ligation kit (purchased from Takara Biotechnology (Dalian) Co., Ltd.). The ligation reaction system was as follows: 1 µl of double enzyme digested and purified product of vector PMV-P1(SacI/XhoI), 5 µl of double enzyme digested and purified product of 3CD gene (SacI/SalI), 6 µl of Solution I and a total 12 µl of reaction system, and the ligation was performed for 1 hour at 16° C. The ligated recombinant expression vectors were transformed into 100 µl of E. coli (DH5α) competent cells, plated on LB+Amp (100 µg/ml) solid medium and cultured in an incubator at 37° C. overnight.

Figure 4A:
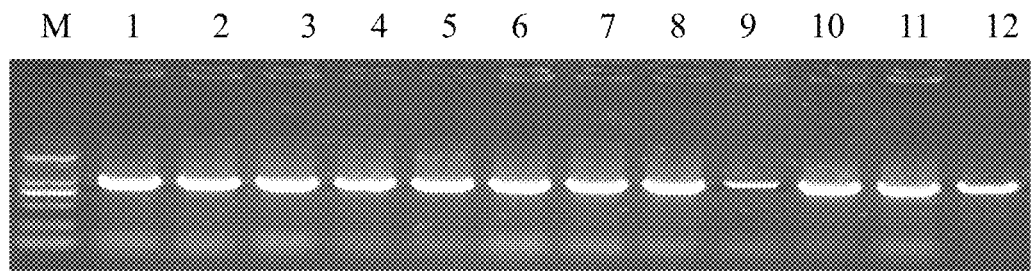
Figure 4B:
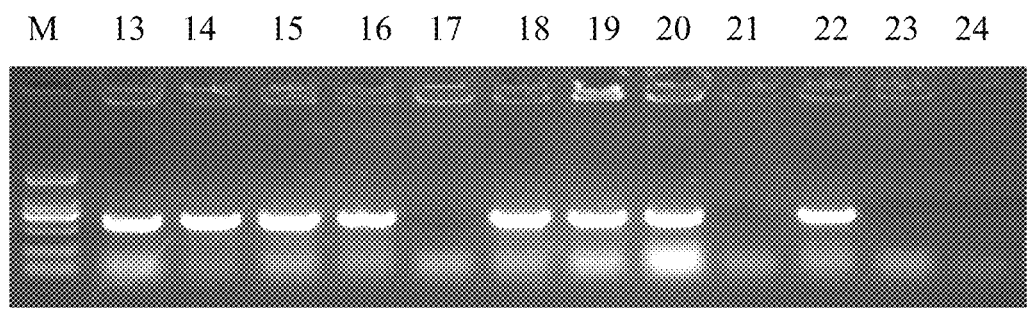
Figure 5:
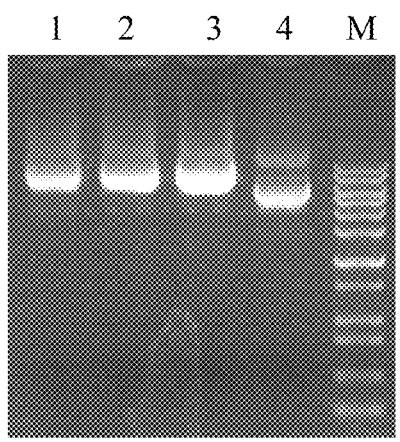
FIG. 5 is result of detection of the extracted recombinant expression plasmid PMV-P1-3CD; wherein, 1-3 are the recombinant expression plasmid PMV-P1-3CD; 4 is the recombinant expression plasmid PMV-P1 as a control; M: DL10000 Plus (Beijing TransGen Biotech Co., Ltd.).
Figure 6:
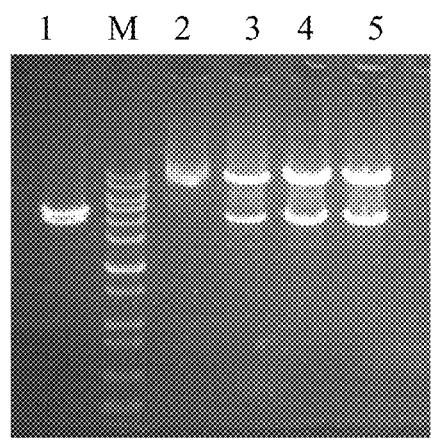
FIG. 6 is electrophoresis result of double enzyme digestion (SacI, SalI) of the recombinant expression plasmid PMV-P1-3CD; 1 is the double enzyme digestion of the recombinant expression plasmid PMV-P1 as a control; 2 is a control for the recombinant expression plasmid PMV-P1-3CD; 3-5 are the double enzyme digestion of the recombinant expression plasmid PMV-P1-3CD; wherein M: DL10000 Plus (Beijing TransGen Biotech Co., Ltd.).
Figure 13:
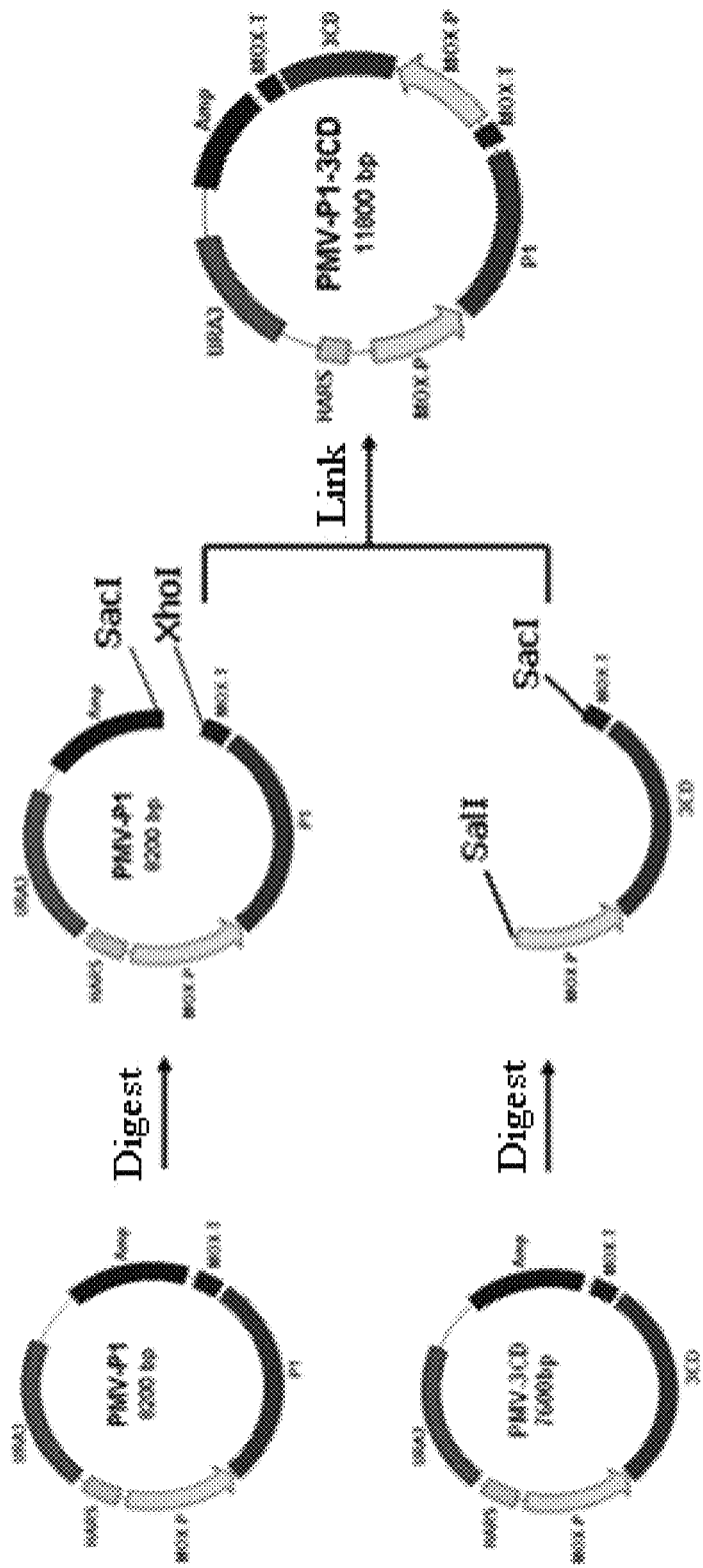

Screen of transformed clones: the transformed clones were identified by PCR by picking monoclonal colonies on a LB+Amp solid medium as a template. The primer sequences of P1 gene were as follows: primer F SEQ ID NO. 15, and primer SEQ ID NO. 16; the primer sequences of 3CD gene were as follows: primer SEQ ID NO. 17, and primer SEQ ID NO. 18. PCR reaction system was as follows: 2 µl of PCR buffer, 2 µl of dNTP, 0.1 µl of primer F, 0.1 µl of primer R, 0.1 µl of Taq DNA polymerase, 15.7 µl of distilled water, and a total volume of 20 µl. Reaction conditions were as follows: 95° C. for 2 min; 95° C. for 30s, 55° C. for 30s, 72° C. for 1 min; performing 30 cycles. The PCR amplified DNA fragments were detected by 1% agarose gel electrophoresis, and the size of the PCR product of P1 gene was about 1000 bp, and the size of the PCR product of 3CD gene was about 630 bp. Results of PCR electrophoresis were shown in FIG. 4a and FIG. 4b. The correct transformed clones identified by PCR were named as recombinant expression vector PMV-P1-3CD, and schematic diagram of the construction of the recombinant expression vectors was shown in FIG. 13. The identified correct clones were inoculated on 10 ml LB+Amp liquid medium, and cultured at 37° C. in a shaker at 200 rpm overnight. The recombinant expression plasmid PMV-P1-3CD was extracted according to the instructions of the plasmid extraction kit (from Beijing TransGen Biotech Co., Ltd.), and the extracted recombinant expression vector was detected by 1% agarose electrophoresis, and the results were shown in FIG. 5. The obtained recombinant expression vector was identified by the enzyme digestion. The enzyme digestion reaction system was as follows: 5 µl of plasmid, 1 µl of each of SacI and Sa/I, 2 µl of 10×K buffer and adding water to 20 µl. The enzyme digestion was performed for 4 hours at 37° C. The results of electrophoresis detection for enzyme digestion were shown in FIG. 6.

Example 3

Inducible Expression and Detection of EV71 Strain Expressed by *Hansenula polymorpha*

A *Hansenula polymorpha* ATCC26012 uracil defective host cell AU-0501 (wildtype host stain was from ATCC26012, and the ATCC26012 uracil defective host cell was obtained by method of gene knockout), with an Accession No. of CGMCC No. 7013, was transformed with the recombinant expression vector PMV-P1-3CD by electroporation.

The transformed clone was screened and identified by selective medium and method of PCR, and the transformed clones containing both P1 and 3CD genes which had been identified were subcultured in the selective medium to obtain a strain AU-PMV-P1-3CD co-expressing P1 protein and 3CD protein. The strain was inoculated in the selective medium MDL (0.67% yeast medium with nitrogen source, purchased from SIGMA-ALDRICH CO. LLC., specification: Y1251-KG, batch no. 030M1754), 0.5% ammonium sulfate, 2% glucose), cultured for 20 hours in a shaker at 33° C. and centrifuged at 5000 rpm for 6 min. The precipitate was collected, added into a induction medium MM (0.67% yeast medium with nitrogen source, 0.5% ammonium sulfate, 1% methanol) with supplementing 1% methanol every day, for inducing expression for 3 days.

SDS-PAGE gel electrophoresis analysis: 100 μl of induced samples were taken and centrifuged, the precipitate was collected, washed with sterile water, treated with NaOH for 3 min and centrifuged. The supernatant was discarded, the precipitate was resuspended in 100 μl SDS sample butter, boiled for 10 min, and centrifuged. 10 μl of supernatant was taken and loaded for electrophoresis. After electrophoresis, the gel was taken down for silver staining and scanned with a gel imaging system software for analysis of the expression level of the target protein.

Figure 7:
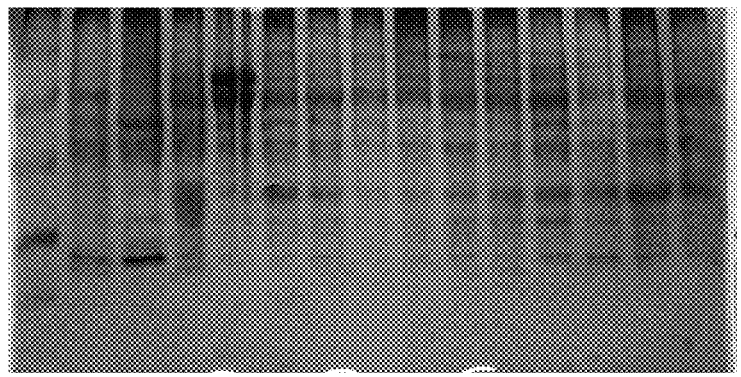
FIG. 7 is detection result of SDS-PAGE of proteins expressed in *Hansenula polymorpha* after the inducible expression of the EV71 strain (PMV-P1-3CD plasmid transformed strain) by a vial of methanol for 72 h; 1 is the prokaryotic expression strain as positive control; 2 is the protein from the host cell without foreign gene (negative control); 3-14 are samples induced by strains; M is a protein marker with low molecular weight (Beijing TransGen Biotech Co., Ltd.).

The results detected by SDS-PAGE show that (see FIG. 7) the molecular weight of proteins expressed by the recombinant strain was about 32.7 KD, consistent with the predicted size of the target protein.

Detection by Western-blot: an anti-EV71-VP1 antibody (AbMax Biotechnology (Beijing) Co., LTD, 22A12) was used as a primary antibody, and an HRP-goat anti-mouse-IgG (Beijing Bioss Biotechnology Co., LTD) was used as a secondary antibody, DAB was used for development.

Figure 8:
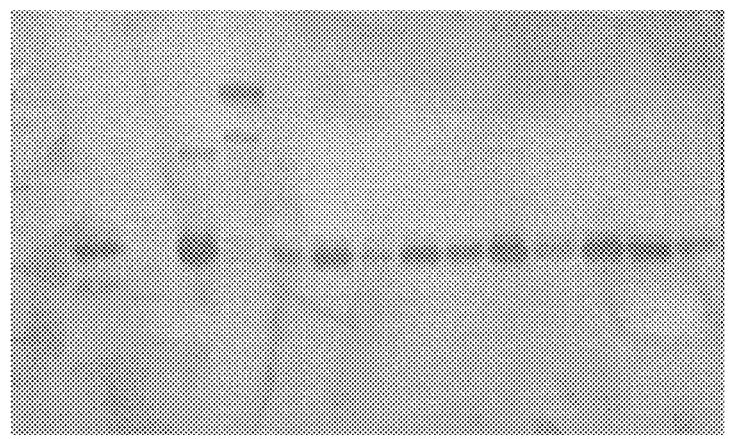
FIG. 8 is detection result of WB of proteins expressed in *Hansenula polymorpha* after the inducible expression of the EV71 strain (PMV-P1-3CD plasmid transformed strain) by a vial of methanol for 72 h; 1 is the prokaryotic expression strain as positive control; 2 is the protein from the host cell without foreign gene (negative control); 3-14 are samples induced by strains; M is a protein marker with low molecular weight (Beijing TransGen Biotech Co., Ltd.).

The results of Western-blot show that (see FIG. 8) the expression product can specifically bind to a monoclonal antibody, and had a more clear reaction band at 32.7 KD, which was in line with the results of SDS-PAGE, indicating that the expression product has good immune reactivity.

Example 4

Fermentation and Culture of the Recombinant EV71 Yeast Expression Strain in a 30 L Fermentation Tank The recombinant *Hansenula polymorpha* strain was inoculated in a 150 ml first-grade seed medium (0.67% yeast medium with nitrogen source (purchased from SIGMA-ALDRICH CO. LLC., specification Y1251-KG, batch No.: 030M1754), 0.5% ammonium sulfate, 2% glucose), and cultured with shaking at 200 rpm for 20 hours in a shaker at 33° C. Then all the culture was inoculated in a 1500 ml second-grade seed medium (0.67% yeast medium with nitrogen source, 0.5% ammonium sulfate, 2% glycerol), and cultured with shaking at 200 rpm for 20 hours in a shaker at 33° C. ($OD_{600nm}$ up to 8-10). Then all the culture was inoculated in a 30 L fermentation tank which contained 15 L fermentation medium (glycerol, ammonium dihydrogen phosphate, potassium chloride, calcium chloride, sodium chloride, magnesium sulfate, sodium ethylene diamine tetracetate, with a mass ratio of 140:70:20:15:2:1). The pH of the fermentation fluid was adjusted by supplementing ammonia water to maintain at 5.0. The fermentation temperature was 30° C., the rotate speed was controlled at 350-750 rpm, the air velocity was 0.5-1.0 m³/h, high density fermentation needs to supplement with pure oxygen, and the dissolved oxygen was controlled at 20-60%. At 20 h, the carbon source in the fermentation medium was depleted and a total 2.0 L of glycerol was added in 5 times with 0.40 L per time. Whenever the carbon source was depleted and the dissolved oxygen increased, glycerol was added. The mycelium grows for a total of about 36 h, and the weight of the wet mycelia was up to about 0.3-0.4 g/ml. At the stage of derepression: rotate speed was 750 rpm, air velocity was 1.0 m³/h, and the dissolved oxygen was controlled at 20-60%, 1 L of mixed solution of glycerol and methanol (400 ml of glycerol, 600 ml of methanol) was added to perform derepression culture at 36-54 h (a total of 16-18 h). At the stage of induction: the methanol induction was carried out at 54-94 h (36-40 h), and the dissolved oxygen was controlled at about 40%. At the end of fermentation: at 92-94 h, when the methanol was consumed completely, the dissolved oxygen was increased to more than 80% and the temperature was cooled to 20° C., the fermentation tank was removed to finish the fermentation, and the weight of the wet mycelia was in the range of 0.3-0.4 g/ml.

Figure 9:
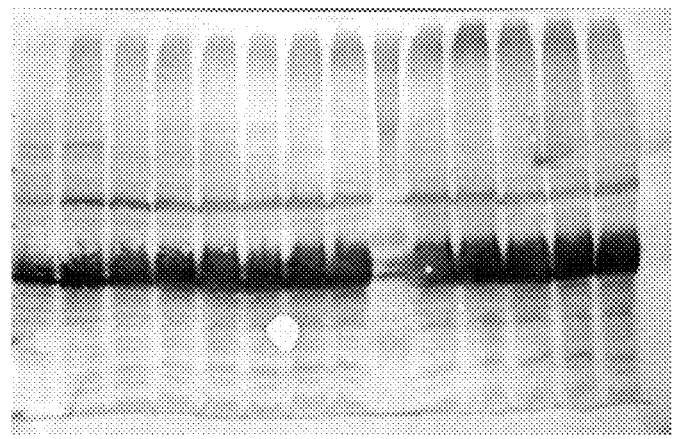
FIG. 9 is detection result of Western blot of proteins expressed in *Hansenula polymorpha* of the EV71 strain samples in different fermentation time (44, 48, 52, 56, 60, 64, 68, 72, 76, 80, 84, 88, 92, 96 hours), M is a protein marker with low molecular weight (Beijing TransGen Biotech Co., Ltd.).
Figure 10:
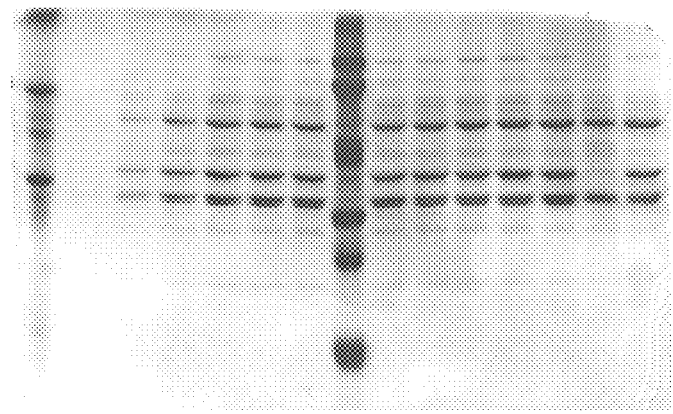
FIG. 10 is detection result of SDS-PAGE of samples ultra-centrifuged and collected in individual tubes; 1 is negative control; 1-14 are samples ultra-centrifuged and collected in individual tubes; M is a protein marker with low molecular weight (Beijing TransGen Biotech Co., Ltd.).
Figure 11:
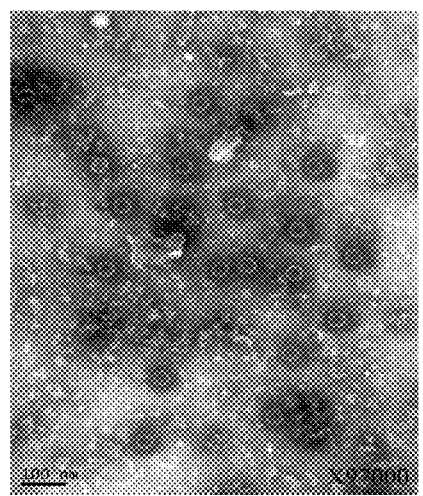
FIG. 11 is a transmission electron microscope photograph of the purified EV71 VLPs (magnification factor: 97000).

Identification of the EV71 VLPs expressed in *Hansenula polymorpha*: the above samples at different fermentation time (44, 48, 52, 56, 60, 64, 68, 72, 76, 80, 84, 88, 92, 96 hours) were taken and used for detection by Western blot using the EV71-VP1 monoclonal antibody (AbMax Biotechnology (Beijing) Co., LTD, 22A12) as a primary antibody and using a HRP-goat anti-mouse-IgG (Bioss Biotechnology Co., LTD) as a secondary antibody, with development with DAB, and the results are shown as FIG. 9.

The results of the Western-blot show that the expression product can specifically bind to the monoclonal antibody, and had a more clear reaction band at 32.7 KD, indicating that the expression product has good immune reactivity.

Determination of the expression level of fermentation of the recombinant EV71 VLPs:

The supernatant collected by centrifugation after cell breakage was diluted in a series of 10 times of dilution, and the expression level of the recombinant EV71 VLP was determined via a EV71 antigen ELISA detection kit (AbMax Biotechnology (Beijing) Co., LTD, this kit mainly detects the EV71-VP1 protein, Lot#100408) using the purified product of EV71-VP1 expressed in a prokaryotic system as standard, and the result was shown in Table 1.

TABLE 1

Detection result of the content of antigen in the fermented and broken liquid (ELISA method)

| | Concentration of standard ng/ml | | | | |
| --- | --- | --- | --- | --- | --- |
| | Standard 1 200 | Standard 2 100 | Standard 3 50 | Standard 4 25 | Standard 5 12.5 |
| $OD_{450\,nm}$ | 2.491 | 1.295 | 0.713 | 0.314 | 0.234 |
| $OD_{450\,nm}$ of sample | 0.509 | 0.502 | average of $OD_{450\,nm}$ | | 0.5055 |
| Calculated concentration ng/ml | 36.02 | Dilution factor | $10^4$ | Concentration of sample μg/ml | 360 |

The results detected by ELISA show that: the expression level of the EV71 VLPs in the fermented and broken cell liquid was 360 mg/L. EV71 expressed by *Hansenula polymorpha* cell had high expression level.

Example 5

Isolation and Purification of EV71 VLPs

Cell breakage: the *Hansenula polymorpha* cells obtained by fermentation in Example 4 were resuspended in the cell lysis buffer (20 mmol/L $NaH_2PO_4$, 2 mmol/L $EDTA-Na_2$, 0.4 mol/L NaCl, pH 7.5) for washing for 2 times, and then suspended in a cell lysis buffer containing 2 mmol/L PMSF, 1% Tween-20, 3% PEG 6000 in a ratio of 1:4 (w/v), and broken twice at a pressure of 1100 bar with a high pressure homogenizer, so as to make the cell broken rate reach more than 95%.

Clarification: the broken cell lysate was poured into a centrifuge bowl, centrifuged for 20 min at 8000 rpm, and the supernatant was collected and microfiltered through a 0.45 μm membrane to remove the macromolecular substances.

Ultrafiltration: the clarified protein solution was ultrafiltered through a 50 KD membrane to remove the small molecule substances.

Precipitation of the virus particles: the ultrafiltered protein solution was adjusted with 0.5M NaOH to pH 6.5, 5M NaCl solution was added into the solution, and 0.5 g/ml PEG 6000 solution was added to the solution in drop-wise under stirring to a final concentration of 0.12 g/ml. The resultant solution stood for 2 h at 4° C., was centrifuged at 12000 rpm for 30 min at 4° C., the supernatant was discarded, and the precipitate was dissolved with proper volume of 20 mmol/L PB and re-centrifuged at 5000 rpm for 30 min at 4° C., and the supernatant obtained by the second centrifugation was collected to obtain the crude pure protein solution.

Ultra-centrifugation: solid potassium bromide is added into the crude pure protein solution to adjust the density to 1.25 g/ml. The order for loading samples for ultracentrifugation was: 150 ml of NaCl-EDTA; 300 ml of 1.25 KBr sample solution; 700 ml of 1.30 KBr gradient solution; 540 ml of 1.35 KBr gradient solution. Ultracentrifugation was performed at 25000 rpm for 4 h at 8° C. 1.35 KBr solution was used as the upper solution to collect the solutions having ultraviolet absorption peaks at UV 280 nm in individual tubes, and the solution in each tube was sampled for detection by SDS-PAGE, and the detection results were shown as FIG. 10.

Molecular sieve chromatography: taking Sephacryl S-500HR as an example, elution was performed with PBS (pH7.0), the eluent having ultraviolet absorption peaks at UV 280 nm were collected to obtain the purified protein solution.

Detection of the concentration of purified proteins (Lowry method): 0 ml, 0.2 ml, 0.4 ml, 0.6 ml, 0.8 ml, 1.0 ml of the standard protein, viz., bovine serum albumin solution (100 μg/ml) were accurately weighted and placed in test tubes respectively, distilled water was added to the tests to 1 ml, meanwhile 1 ml of 4-fold diluted purified protein solution was added into the test tubes, and 5 ml alkaline copper solution and 0.5 ml phenol reagent were added into the test tubes respectively, for determining the absorbance value at 650 nm of wave length in cuvettes. The standard curve was plotted using the protein content of the standard protein as abscissa and the absorbance value as coordinate, and the concentration of the purified protein to be detected was calculated. The detection results were shown as Table 2.

TABLE 2

Detection results of the concentration of the purified protein (Lowry method)

| | Concentration of standard μg/ml | | | | |
|---|---|---|---|---|---|
| | Standard 1 20 | Standard 2 40 | Standard 3 60 | Standard 4 80 | Standard 5 100 |
| $OD_{650\ nm}$ | 0.052 | 0.118 | 0.176 | 0.237 | 0.285 |
| $OD_{650\ nm}$ of sample | 0.150 | 0.147 | average of $OD_{650\ nm}$ | | 0.1485 |
| Calculated concentration μg/ml | 51.86 | final concentration of the purified protein solution μg/ml | | 207 | |

The final concentration of the purified protein obtained according to the detection results of Lowry method was 207 μg/ml.

Electronic microscope analysis for the purified protein: 10 ul of purified EV71 protein solution was added drop-wise onto the copper grid, kept away from light for 5 min, the extra liquid was removed completely. Then the purified EV71 protein solution was stained with 1% phosphotungstic acid for 2 min and the EV71 VLPs were analyzed through a transmission electron microscope (TEM). The results indicate that the EV71 protein appeared as a VLP, had a icosahedron structure of the naturally occurring virus with a particle size of around 30 nm, and the particle was integral and regular (as shown in FIG. 11, magnification factor: 97000).

Example 6

Preparation of EV71 VLPs Vaccine by Aluminium Phosphate Adsorption In Situ Method Control of the main indexes: the content of the antigen (EV71 VLP) was 20 μg/ml; the content of aluminium was controlled at 0.45-0.60 mg/ml; and the pH value was controlled at 5.8-6.0.

Preparation method: the sterilized and filtered sodium chloride solution, $AlCl_3$ solution, and EV71 VLPs were added in a sterile- and pyrogen-free reactor successively, stirred with a magnetic stirrer, and after stirring well the mixed solution of NaOH and phosphate was added in a proper constant speed flow to initiate the adsorption reaction in situ while adjusting the pH value. The acceleration of flow should not too fast, and was controlled at 2-5 ml/min to enable the adsorption reaction to take place at a relatively constant pH value. When pH was 5.8-6.0, the addition of the mixed solution of NaOH and phosphate was stopped. Stirring was performed for 30 min, sampling was performed for testing pH value, the adsorption reaction was ended and the preparation of the vaccine was completed. The test standard and test results of the prepared vaccine were shown in Table 3.

TABLE 3

Test results of EV71 VLP vaccine prepared by aluminium phosphate adsorption in situ method

| Test items | Content of aluminium | pH value | Adsorption rate |
|---|---|---|---|
| Test criteria | 《Chinese Pharmacopoeia》Volume III, Appendix VII F Testing method of aluminium hydroxide | 《Chinese Pharmacopoeia》Volume III, Appendix V A Testing method of pH value | refer to《Chinese Pharmacopoeia》Volume III, Appendix X A |
| Test standard | 0.45-0.60 mg/ml | 5.8-6.0 | >95% |
| Test results | 0.55 mg/ml | 5.83 | 99.3% |

The results in Table 3 show that: all the test indexes of the EV71 VLP vaccine prepared by aluminium phosphate adsorption in situ method meet with the test standard.

Example 7

Immunogenicity ($ED_{50}$) Test of the Vaccine Prepared from EV71 VLPs

Vaccine sample: EV71 VLP vaccine containing an aluminium phosphate adjuvant prepared in the Example 6.

Experimental animals: 60 SPF grade BALB/c mice with a weight 18-22 g per mouse were chosen as experimental animals, which were purchased from Beijing Vital River Laboratory Animal Technology Co., Ltd.

Immune procedure: the prepared vaccine was diluted to 0.5, 0.25, 0.125, 0.0625, 0.03125 μg/ml in a series of doubling dilution, each dilution was injected intraperitoneally into 10 mice with each mouse receiving 1 ml. 30 days after immunization, blood was collected from the eyeballs of mice. The collected blood was placed at 37° C. for 2 h, centrifuged at 4000 g for 10 min, and the supernatant was sucked out as antiserum to be detected.

Detection of the antiserum by indirect ELISA method: each of the purified antigen solutions in Example 5 was diluted with coating buffer to a concentration of 1 μg/ml and the dilution was added into the shrinkage pool of a 96 well microplate reader and incubated at 4° C. overnight. After removing the coating buffer completely, the microplate reader was washed by filling with the cleaning solution PBST. The microplate reader was filled with blocking buffer (1% BSA in PBST) and incubated for 1 hour at 37° C. After removing the blocking buffer completely, 100 μl of antiserum to be detected was added into each well, and incubated for 1 hour at 37° C. After removing the serum liquid completely, the microplate reader was washed for 3 times by filing with cleaning solution PBST. 100 μl of HRP labeled goat-anti-mouse IgG (in 1:4000 dilution) was added into each well and incubated for 1 hour at 37° C. After removing the liquid from microplate completely, the microplate reader was washed for 3 times by filing with cleaning solution PBST. 100 μl TMB developing solution was added into each well, and protected from light for 15 min at 37° C. To each well, 50 μl of 2M $H_2SO_4$ was added for completion. $OD_{450nm}$ value was determined by ELISA instrument.

The detection results of the antiserum by indirect ELISA were shown in Table 4.

TABLE 4

Detection result of the antiserum by indirect ELISA method

| | Conc. | | | | | | |
|---|---|---|---|---|---|---|---|
| No. | 0.5 μg/ml | 0.25 μg/ml | 0.125 μg/ml | 0.0625 μg/ml | 0.03125 μg/ml | Negative serum | Positive control |
| 1 | 0.810 | 3.003 | 1.094 | 0.195 | 0.083 | 0.051 | 3.009 |
| 2 | 1.742 | 1.678 | 2.349 | 0.096 | 0.055 | 0.049 | 3.013 |
| 3 | 2.144 | 0.783 | 0.107 | 0.729 | 0.092 | — | — |
| 4 | 2.902 | 2.192 | 1.448 | 1.051 | 0.101 | — | — |
| 5 | 2.650 | 0.372 | 0.205 | 0.103 | 0.822 | — | — |
| 6 | 1.815 | 1.545 | 1.338 | 0.301 | 1.038 | — | — |
| 7 | 1.633 | 2.232 | 2.051 | 2.009 | 0.058 | — | — |
| 8 | 2.589 | 1.351 | 0.793 | 1.473 | 0.078 | — | — |
| 9 | 1.988 | 1.628 | 0.098 | 0.098 | 0.109 | — | — |
| 10 | 1.902 | 2.749 | 0.229 | 0.672 | 0.991 | — | — |
| Positive rate | 100% | 100% | 80% | 70% | 30% | — | — |

According the detection results, the positive conversion rate of an antibody was shown as Table 5.

TABLE 5

Calculated result of the positive conversion rate of an antibody

| Content of antigen (μg/ml) | Antibody of mouse | | positive conversion rate | Sum up | | positive conversion rate |
|---|---|---|---|---|---|---|
| | positive | negative | | positive | negative | |
| 0.5 | 10 | 0 | 100% | 38 | 0 | 100% |
| 0.25 | 10 | 0 | 100% | 28 | 0 | 100% |
| 0.125 | 8 | 2 | 80% | 18 | 2 | 90.0% |
| 0.0625 | 7 | 3 | 70% | 10 | 5 | 66.67% |
| 0.03125 | 3 | 7 | 30% | 3 | 12 | 20.0% |

Calculated in accordance with Reed-Muench method: $ED_{50}$=0.049 (μg)

It can be seen from the experimental results obtained by mice $ED_{50}$ that: when only 0.049 μg of EV71 VLP vaccine prepared according to the present invention was used to immune the mice, the positive conversion rate of the antibody can reach 50%. Therefore, the EV71 VLPs of the present invention had strong immunogenicity.

Example 8

Abnormal Toxicity Test of the Vaccine Prepared from EV71 VLPs

Vaccine sample: EV71 VLP vaccine containing an aluminium phosphate adjuvant prepared in Example 6.

Experimental animals: 5 SPF grade BALB/c mice with a weight of 18-22 g per mouse, and 2 SPF grade Hartley guinea pig with a weight of 250-350 g per guinea pig were purchased from Beijing Vital River Laboratory Animal Technology Co., Ltd.

Experimental method: every experimental animal was weighted before injection with the mouse being 18-22 g and the guinea pig being 250-350 g. 5 mice were intraperitoneally injected with vaccines in the amount of 0.5 ml/mouse, 2 guinea pigs were intraperitoneally injected with vaccines in the amount of 5.0 ml/guinea pig, and then the experimental animals were observed for 7 days. Meanwhile, the same batch of experimental animals were used as blank control. Criterion of acceptability: the blank control and the experimental animals were healthy and had no abnormal reactions during the observation period, and every experimental animal had a weight gain at end. The details for animal experiments were shown in Table 6.

TABLE 6

Details for animal experiments

| Species of animals | No. | Labeled position | Initial weight (g) | Final weight (g) |
|---|---|---|---|---|
| Experimental group of mice | 1 | Head | 18.5 | 19.6 |
| | 2 | Spine | 19.0 | 20.3 |
| | 3 | Tail | 18.6 | 19.5 |
| | 4 | Leg | 19.6 | 21.5 |
| | 5 | None | 19.2 | 20.9 |
| Experimental group of guinea pig | 1 | Head | 338.7 | 360.8 |
| | 2 | Spine | 357.0 | 403.6 |
| Control group of mice | 1 | Head | 19.4 | 20.8 |
| | 2 | Spine | 19.7 | 21.3 |
| | 3 | Tail | 19.0 | 19.6 |
| | 4 | Leg | 18.5 | 20.7 |
| | 5 | None | 18.9 | 19.9 |
| Control group of guinea pig | 1 | Head | 336.2 | 376.3 |
| | 2 | Spine | 340.3 | 399.6 |

Conclusion: the blank control and the experimental animals were healthy and had no abnormal reactions during the observation period, and every experimental animal had a weight gain on day 8. It was demonstrated that vaccines prepared from EV71 VLPs had no abnormal toxicity and the experimental animals had good safety.

While the present invention has been described in detail through general description and specific embodiments above, it is obvious to a person skilled in the art that some modifications or improvements can be made on the basis of the present invention. Therefore, all these modifications or improvements made without departing from the spirit of the present invention belong to the scope claimed in the present invention.

INDUSTRIAL APPLICABILITY

The present invention provides EV71 VLPs and a preparation method and application thereof. The method comprises: connecting a P1 protein gene and a 3CD protease gene of an EV71 virus with a PMV plasmid to construct a PMV-P1-3CD recombinant expression plasmid; then transforming a Hansenula polymorpha AU-0501 expression strain with the PMV-P1-3CD recombinant expression plasmid to obtain an AU-PMV-P1-3CD recombinant expression strain; fermenting and culturing the recombinant expression strain, and inducing the strain to express the EV71 VLP protein with methanol; centrifuging and collecting cells for homogeneous breakage at a high pressure; and purifying the supernatant through ion-exchange chromatography, hydrophobic chromatography, and molecular sieve chromatography and the like to obtain EV71 VLPs.

The EV71 VLP vaccine provided in the present invention has excellent immunogenicity, safety, immunological property and biological activity, and it can be prepared and purified in a large scale and used for preparing vaccines for preventing EV71 infection, and thus has good economic value and application prospect.

What is claimed is:

1. A recombinant expression vector, comprising P1 gene and 3CD gene of EV71 virus, wherein the expression vector is PMV-P1-3CD, and
wherein the P1 gene of the EV71 virus has a nucleotide sequence as shown in SEQ ID No. 1 or the 3CD gene of the EV71 virus has a nucleotide sequence as shown in SEQ ID No. 3.

2. A host cell comprising the recombinant expression vector according to claim 1.

3. The recombinant expression vector according to claim 1, wherein the P1 gene of the EV71 virus has a nucleotide sequence as shown in SEQ ID No. 1.

4. A host cell comprising the recombinant expression vector according to claim 3.

5. The recombinant expression vector according to claim 1, wherein the 3CD gene of the EV71 virus has a nucleotide sequence as shown in SEQ ID No. 3.

6. A host cell comprising the recombinant expression vector according to claim 5.

7. The recombinant expression vector according to claim 1, comprising a methanol oxidase promoter or a formaldehyde dehydrogenase promoter.

8. A host cell comprising the recombinant expression vector according to claim 7.

9. A method of preparing a compostion, comprising:
transforming an expression strain with the recombinant expression vector according to claim 1 to obtain a recombinant expression strain;
fermenting and culturing the recombinant expression strain;
isolating and purifying EV71 virus-like particles; and
absorbing the EV71 virus-like particles with an aluminum phosphate adjuvant to prepare the EV71 viral vaccine.

10. The method of claim 9, wherein the recombinant expression strain is AU-PMV-P1-3CD.

11. The method of claim 9, wherein the expression strain is *Hansenula polymorpha* AU-0501.

12. EV71 virus-like particles, wherein the EV71 virus-like particles are prepared by the steps of:
(1) transforming a *Hansenula polymorpha* AU-0501 expression strain with the PMV-P1-3CD recombinant expression vector to obtain an AU-PMV-P1-3CD recombinant expression strain;
(2) fermenting and culturing the recombinant expression strain;
(3) isolating and purifying the EV71 virus-like particles, further comprising centrifuging and collecting mycelia for homogeneous breakage, clarifying, ultrafiltering, and precipitating the virus particles, ultracentrifuging, and collecting the supernatant, purifying the supernatant through ion-exchange chromatography, hydrophobic chromatography or molecular sieve chromatography, wherein the PMV-P1-3CD recombinant expression vector comprises a P1 gene of the EV71 virus having a nucleotide sequence as shown in SEQ ID No. 1 or a 3CD gene of the EV71 virus having a nucleotide sequence as shown in SEQ ID No. 3.

13. A hand, foot and mouth disease vaccine, comprising virus-like particles prepared from the process of claim 12.

14. A method for preparing the vaccine according to claim 13, further comprising absorbing the EV71 virus-like particles with an aluminum phosphate adjuvant to prepare a vaccine comprising 20 µg/ml virus-like particles.

* * * * *

SEQUENCE LISTING

<160> NUMBER OF SEQ ID NOS: 18

<210> SEQ ID NO 1
<211> LENGTH: 2592
<212> TYPE: DNA
<213> ORGANISM: Enterovirus 71

<400> SEQUENCE: 1

```
atgggttctc aggtgtctac ccagagatcc ggttctcacg agaactctaa ctctgccacc        60
gagggttcta ccatcaacta caccaccatc aactactaca aggactctta cgccgccacc       120
gccggtaagc agtctctgaa gcaggaccca gacaagttcg ccaacccagt gaaggacatc       180
ttcaccgaga tggccgcccc actgaagtct ccatctgccg aggcctgcgg ttactctgac       240
agagtggccc agctgaccat cggtaactct accatcacca cccaggaggc cgccaacatc       300
atcgtgggtt acggtgagtg gccatcttac tgctctgact ctgacgccac cgccgtggac       360
aagccaacca gaccagacgt gtctgtgaac agattctaca ccctggacac caagctgtgg       420
gagaagtctt ctaagggttg gtactggaag ttcccagacg tgctgaccga gaccggtgtg       480
ttcggtcaga acgcccagtt ccactacctg tacagatccg gtttctgcat ccacgtgcag       540
tgcaacgcct ctaagttcca ccagggtgcc ctgctggtgg ccgtgctgcc agagtacgtg       600
atcggtaccg tggccggtgg taccggtacc gaggacaccc acccaccata caagcagacc       660
```

| | |
|---|---:|
| cagccaggtg ccgacggttt cgagctgcag cacccatacg tgctggacgc cggtatccca | 720 |
| atctctcagc tgaccgtgtg cccacaccag tggatcaacc tgagaaccaa caactgcgcc | 780 |
| accatcatcg tgccatacat caacgccctg ccattcgact ctgccctgaa ccactgcaac | 840 |
| ttcggtctgc tggtggtgcc aatctctcca ctggactacg accagggtgc cacccagtg | 900 |
| atcccaatca ccatcaccct ggccccaatg tgctctgagt tcgccggtct gagacaggcc | 960 |
| gtgacccagg gtttcccaac cgagctgaag ccaggtacca accagttcct gaccaccgac | 1020 |
| gacggtgtgt ctgccccaat cctgccaaac ttccacccaa cccatgcat ccacatccca | 1080 |
| ggtgaggtga aaacctgct ggagctgtgc caggtggaga ccatcctgga ggtgaacaac | 1140 |
| gtgccaacca acgccaccctc tctgatggag agactgagat tcccagtgtc tgcccaggcc | 1200 |
| ggtaagggtg agctgtgcgc cgtgttcaga gccgacccag gtagaaacgg tccatggcag | 1260 |
| tctaccctgc tgggtcagct gtgcggttac tacacccagt ggtctggttc tctggaggtg | 1320 |
| accttcatgt tcaccggttc tttcatggcc accggtaaga tgctgatcgc ctacacccca | 1380 |
| ccaggtggtc cactgccaaa ggacagagcc accgccatgc tgggtaccca cgtgatctgg | 1440 |
| gacttcggtc tgcagtcttc tgtgaccctg gtgatcccat ggatctctaa cacccactac | 1500 |
| agagcccacg ccagagacgg tgtgttcgac tactacacca ccggtctggt gtctatctgg | 1560 |
| taccagacca actacgtggt gccaatcggt gccccaaaca ccgcctacat catcgccctg | 1620 |
| gccgccgccc agaagaactt caccatgaag ctgtgcaagg acgcctctga catcctgcag | 1680 |
| accggtacca tccagggtga cagagtggcc gacgtgatcg agtcttctat cggtgactct | 1740 |
| gtgtctagag ccctgaccca cgccctgcca gccccaaccg tcagaacac ccaggtgtct | 1800 |
| tctcacagac tggacaccgg taaggtgcca gccctgcagg ccgccgagat cggtgcctct | 1860 |
| tctaacgcct ctgacgagtc tatgatcgag accagatgcg tgctgaactc tcactctacc | 1920 |
| gccgagacca ccctggactc tttcttctct agagccggtc tggtgggtga atcgacctg | 1980 |
| ccactggagg gtaccaccaa cccaaacggt tacgccaact gggacatcga catcaccggt | 2040 |
| tacgcccaga tgagaagaaa ggtggagctg ttcacctaca tgagattcga cgccgagttc | 2100 |
| accttcgtgg cctgcacccc aaccggtgag gtggtgccac agctgctgca gtacatgttc | 2160 |
| gtgccaccag gtgccccaaa gccagactct agagagtctc tggcctggca gaccgccacc | 2220 |
| aacccatctg tgttcgtgaa gctgtctgac ccaccagccc aggtgtctgt gccattcatg | 2280 |
| tctccagcct ctgcctacca gtggttctac gacggttacc caaccttcgg tgagcacaag | 2340 |
| caggagaagg acctggagta cggtgcctgc ccaaacaaca tgatgggtac cttctctgtg | 2400 |
| agaaccgtgg gtacctctaa gtctaagtac ccactggtgg tgagaatcta catgagaatg | 2460 |
| aagcacgtga gagcctggat tccaagacca atgagaaacc agaactacct gttcaaggcc | 2520 |
| aacccaaact acgccggtaa ctctatcaag ccaaccggtg cctctagaac cgccatcacc | 2580 |
| accctgtaat ag | 2592 |

```
<210> SEQ ID NO 2
<211> LENGTH: 862
<212> TYPE: PRT
<213> ORGANISM: Enterovirus 71

<400> SEQUENCE: 2
```

Met Gly Ser Gln Val Ser Thr Gln Arg Ser Gly Ser His Glu Asn Ser
 1 5 10 15

Asn Ser Ala Thr Glu Gly Ser Thr Ile Asn Tyr Thr Thr Ile Asn Tyr
20 25 30

```
Tyr Lys Asp Ser Tyr Ala Ala Thr Ala Gly Lys Gln Ser Leu Lys Gln
             35                  40                  45

Asp Pro Asp Lys Phe Ala Asn Pro Val Lys Asp Ile Phe Thr Glu Met
 50                  55                  60

Ala Ala Pro Leu Lys Ser Pro Ser Ala Glu Ala Cys Gly Tyr Ser Asp
 65                  70                  75                  80

Arg Val Ala Gln Leu Thr Ile Gly Asn Ser Thr Ile Thr Thr Gln Glu
                 85                  90                  95

Ala Ala Asn Ile Ile Val Gly Tyr Gly Glu Trp Ser Tyr Cys Ser
                100                 105                 110

Asp Ser Asp Ala Thr Ala Val Asp Lys Pro Thr Arg Pro Asp Val Ser
                115                 120                 125

Val Asn Arg Phe Tyr Thr Leu Asp Thr Lys Leu Trp Glu Lys Ser Ser
            130                 135                 140

Lys Gly Trp Tyr Trp Lys Phe Pro Asp Val Leu Thr Glu Thr Gly Val
145                 150                 155                 160

Phe Gly Gln Asn Ala Gln Phe His Tyr Leu Tyr Arg Ser Gly Phe Cys
                165                 170                 175

Ile His Val Gln Cys Asn Ala Ser Lys Phe His Gln Gly Ala Leu Leu
            180                 185                 190

Val Ala Val Leu Pro Glu Tyr Val Ile Gly Thr Val Ala Gly Gly Thr
            195                 200                 205

Gly Thr Glu Asp Thr His Pro Pro Tyr Lys Gln Thr Gln Pro Gly Ala
    210                 215                 220

Asp Gly Phe Glu Leu Gln His Pro Tyr Val Leu Asp Ala Gly Ile Pro
225                 230                 235                 240

Ile Ser Gln Leu Thr Val Cys Pro His Gln Trp Ile Asn Leu Arg Thr
                245                 250                 255

Asn Asn Cys Ala Thr Ile Ile Val Pro Tyr Ile Asn Ala Leu Pro Phe
            260                 265                 270

Asp Ser Ala Leu Asn His Cys Asn Phe Gly Leu Leu Val Val Pro Ile
        275                 280                 285

Ser Pro Leu Asp Tyr Asp Gln Gly Ala Thr Pro Val Ile Pro Ile Thr
    290                 295                 300

Ile Thr Leu Ala Pro Met Cys Ser Glu Phe Ala Gly Leu Arg Gln Ala
305                 310                 315                 320

Val Thr Gln Gly Phe Pro Thr Glu Leu Lys Pro Gly Thr Asn Gln Phe
                325                 330                 335

Leu Thr Thr Asp Asp Gly Val Ser Ala Pro Ile Leu Pro Asn Phe His
            340                 345                 350

Pro Thr Pro Cys Ile His Ile Pro Gly Glu Val Arg Asn Leu Leu Glu
            355                 360                 365

Leu Cys Gln Val Glu Thr Ile Leu Glu Val Asn Asn Val Pro Thr Asn
    370                 375                 380

Ala Thr Ser Leu Met Glu Arg Leu Arg Phe Pro Val Ser Ala Gln Ala
385                 390                 395                 400

Gly Lys Gly Glu Leu Cys Ala Val Phe Arg Ala Asp Pro Gly Arg Asn
                405                 410                 415

Gly Pro Trp Gln Ser Thr Leu Leu Gly Gln Leu Cys Gly Tyr Tyr Thr
            420                 425                 430

Gln Trp Ser Gly Ser Leu Glu Val Thr Phe Met Phe Thr Gly Ser Phe
            435                 440                 445
```

```
Met Ala Thr Gly Lys Met Leu Ile Ala Tyr Thr Pro Gly Gly Pro
    450                 455                 460

Leu Pro Lys Asp Arg Ala Thr Ala Met Leu Gly Thr His Val Ile Trp
465                 470                 475                 480

Asp Phe Gly Leu Gln Ser Ser Val Thr Leu Val Ile Pro Trp Ile Ser
                    485                 490                 495

Asn Thr His Tyr Arg Ala His Ala Arg Asp Gly Val Phe Asp Tyr Tyr
                500                 505                 510

Thr Thr Gly Leu Val Ser Ile Trp Tyr Gln Thr Asn Tyr Val Val Pro
            515                 520                 525

Ile Gly Ala Pro Asn Thr Ala Tyr Ile Ile Ala Leu Ala Ala Ala Gln
530                 535                 540

Lys Asn Phe Thr Met Lys Leu Cys Lys Asp Ala Ser Asp Ile Leu Gln
545                 550                 555                 560

Thr Gly Thr Ile Gln Gly Asp Arg Val Ala Asp Val Ile Glu Ser Ser
                565                 570                 575

Ile Gly Asp Ser Val Ser Arg Ala Leu Thr His Ala Leu Pro Ala Pro
                580                 585                 590

Thr Gly Gln Asn Thr Gln Val Ser Ser His Arg Leu Asp Thr Gly Lys
            595                 600                 605

Val Pro Ala Leu Gln Ala Ala Glu Ile Gly Ala Ser Ser Asn Ala Ser
610                 615                 620

Asp Glu Ser Met Ile Glu Thr Arg Cys Val Leu Asn Ser His Ser Thr
625                 630                 635                 640

Ala Glu Thr Thr Leu Asp Ser Phe Phe Ser Arg Ala Gly Leu Val Gly
                645                 650                 655

Glu Ile Asp Leu Pro Leu Glu Gly Thr Thr Asn Pro Asn Gly Tyr Ala
                660                 665                 670

Asn Trp Asp Ile Asp Ile Thr Gly Tyr Ala Gln Met Arg Arg Lys Val
            675                 680                 685

Glu Leu Phe Thr Tyr Met Arg Phe Asp Ala Glu Phe Thr Phe Val Ala
    690                 695                 700

Cys Thr Pro Thr Gly Glu Val Val Pro Gln Leu Leu Gln Tyr Met Phe
705                 710                 715                 720

Val Pro Pro Gly Ala Pro Lys Pro Asp Ser Arg Glu Ser Leu Ala Trp
                725                 730                 735

Gln Thr Ala Thr Asn Pro Ser Val Phe Val Lys Leu Ser Asp Pro Pro
                740                 745                 750

Ala Gln Val Ser Val Pro Phe Met Ser Pro Ala Ser Ala Tyr Gln Trp
                755                 760                 765

Phe Tyr Asp Gly Tyr Pro Thr Phe Gly Glu His Lys Gln Glu Lys Asp
    770                 775                 780

Leu Glu Tyr Gly Ala Cys Pro Asn Asn Met Met Gly Thr Phe Ser Val
785                 790                 795                 800

Arg Thr Val Gly Thr Ser Lys Ser Lys Tyr Pro Leu Val Val Arg Ile
                805                 810                 815

Tyr Met Arg Met Lys His Val Arg Ala Trp Ile Pro Arg Pro Met Arg
                820                 825                 830

Asn Gln Asn Tyr Leu Phe Lys Ala Asn Pro Asn Tyr Ala Gly Asn Ser
                835                 840                 845

Ile Lys Pro Thr Gly Ala Ser Arg Thr Ala Ile Thr Thr Leu
850                 855                 860
```

<210> SEQ ID NO 3
<211> LENGTH: 1944
<212> TYPE: DNA
<213> ORGANISM: Enterovirus 71

<400> SEQUENCE: 3

| | | | | | |
|---|---|---|---|---|---|
| atgggtccat | ctctggactt | cgccctgtct | ctgctgagaa | gaaacatcag | acaggtgcag | 60 |
| accgaccagg | gtcacttcac | catgctgggt | gtgagagaca | gactggccgt | gctgccaaga | 120 |
| cactctcagc | caggtaagac | catctggatc | gagcacaagc | tggtgaacgt | gctggacgcc | 180 |
| gtggagctgg | tggacgagca | gggtgtgaac | ctggagctga | ccctgatcac | cctggacacc | 240 |
| aacgagaagt | tcagagacat | caccaagttc | atcccagaga | acatctctac | cgcctctgac | 300 |
| gccaccctgg | tgatcaacac | cgagcacatg | ccatctatgt | tcgtgccagt | gggtgacgtg | 360 |
| gtgcagtacg | gttcctgaa | cctgtctggt | aagccaaccc | acagaaccat | gatgtacaac | 420 |
| ttcccaacca | aggccggtca | gtgcggtggt | gtggtgacct | ctgtgggtaa | ggtggtgggt | 480 |
| atccacatcg | gtggtaacgg | tagacagggt | ttctgcgccg | gtctgaagag | atcctacttc | 540 |
| gcctctgagc | agggtgagat | ccagtgggtg | aagccaaaca | aggagaccgg | tagactgaac | 600 |
| atcaacggtc | caaccagaac | caagctggag | ccatctgtgt | tccacgacat | cttcgagggt | 660 |
| aacaaggagc | cagccgtgct | gcactctaag | gacccaagac | tggaggtgga | cttcgagcag | 720 |
| gccctgttct | ctaagtacgt | gggtaacacc | ctgcacgagc | cagacgagta | catcaaggag | 780 |
| gccgccctgc | actacgccaa | ccagctgaag | cagctggaga | tcaacacctc | tcagatgtct | 840 |
| atggaggagg | cctgctacgg | taccgagaac | ctggaggcca | tcgacctgca | cacctctgcc | 900 |
| ggttacccat | actctgccct | gggtatcaag | aagagagaca | tcctggaccc | aaccaccaga | 960 |
| gacgtgtcta | gaatgaagtt | ctacatggac | aagtacggtc | tggacctgcc | atactctacc | 1020 |
| tacgtgaagg | acgagctgag | atccatcgac | aagatcaaga | agggtaagtc | tagactgatc | 1080 |
| gaggcctctt | ctctgaacga | ctctgtgtac | ctgagaatgg | ccttcggtca | cctgtacgag | 1140 |
| gccttccacg | ccaacccagg | taccatcacc | ggttctgccg | tgggttgcaa | cccagacacc | 1200 |
| ttctggtcta | gctgccaat | cctgctgcca | ggttctctgt | tcgccttcga | ctactctggt | 1260 |
| tacgacgcct | ctctgtctcc | agtgtggttc | agagccctgg | agctggtgct | gagagagatc | 1320 |
| ggttactctg | aggaggccat | ctctctgatc | gagggtatca | accacaccca | ccacgtgtac | 1380 |
| agaaacaaga | cctactgcgt | gctgggtggt | atgccatctg | gttgctctgg | tacctctatc | 1440 |
| ttcaactcta | tgatcaacaa | catcatcatc | agagccctgc | tgatcaagac | cttcaagggt | 1500 |
| atcgacctgg | acgagctgaa | catggtggcc | tacggtgacg | acgtgctggc | ctcttacccg | 1560 |
| ttcccaatcg | actgcctgga | gctggccaag | accggtaagg | agtacggtct | gaccatgacc | 1620 |
| ccagccgaca | agtctccatg | cttcaacgag | gtgaactggg | gtaacgccac | cttcctgaag | 1680 |
| agaggtttcc | tgccagacga | gcagttccca | ttcctgatcc | acccaaccat | gccaatgaga | 1740 |
| gagatccacg | agtctatcag | atggaccaag | gacgccagaa | acacccagga | ccacgtgaga | 1800 |
| tccctgtgcc | tgctggcctg | gcacaacggt | aagcaggagt | acgagaagtt | cgtgtctacc | 1860 |
| atcagatccg | tgccagtggg | tagagccctg | gccatcccaa | actacgagaa | cctgagaaga | 1920 |
| aactggctgg | agctgttcta | atag | | | | 1944 |

<210> SEQ ID NO 4
<211> LENGTH: 646
<212> TYPE: PRT
<213> ORGANISM: Enterovirus 71

-continued

<400> SEQUENCE: 4

```
Met Gly Pro Ser Leu Asp Phe Ala Leu Ser Leu Leu Arg Arg Asn Ile
1               5                   10                  15

Arg Gln Val Gln Thr Asp Gln Gly His Phe Thr Met Leu Gly Val Arg
            20                  25                  30

Asp Arg Leu Ala Val Leu Pro Arg His Ser Gln Pro Gly Lys Thr Ile
        35                  40                  45

Trp Ile Gln His Lys Leu Val Asn Val Leu Asp Ala Val Gln Leu Val
    50                  55                  60

Asp Gln Gln Gly Val Asn Leu Gln Leu Thr Leu Ile Thr Leu Asp Thr
65                  70                  75                  80

Asn Gln Lys Phe Arg Asp Ile Thr Lys Phe Ile Pro Gln Asn Ile Ser
                85                  90                  95

Thr Ala Ser Asp Ala Thr Leu Val Ile Asn Thr Gln His Met Pro Ser
            100                 105                 110

Met Phe Val Pro Val Gly Asp Val Val Gln Tyr Gly Phe Leu Asn Leu
        115                 120                 125

Ser Gly Lys Pro Thr His Arg Thr Met Met Tyr Asn Phe Pro Thr Lys
    130                 135                 140

Ala Gly Gln Cys Gly Gly Val Val Thr Ser Val Gly Lys Val Val Gly
145                 150                 155                 160

Ile His Ile Gly Gly Asn Gly Arg Gln Gly Phe Cys Ala Gly Leu Lys
                165                 170                 175

Arg Ser Tyr Phe Ala Ser Gln Gln Gly Gln Ile Gln Trp Val Lys Pro
            180                 185                 190

Asn Lys Gln Thr Gly Arg Leu Asn Ile Asn Gly Pro Thr Arg Thr Lys
        195                 200                 205

Leu Gln Pro Ser Val Phe His Asp Ile Phe Gln Gly Asn Lys Gln Pro
    210                 215                 220

Ala Val Leu His Ser Lys Asp Pro Arg Leu Gln Val Asp Phe Gln Gln
225                 230                 235                 240

Ala Leu Phe Ser Lys Tyr Val Gly Asn Thr Leu His Gln Pro Asp Gln
                245                 250                 255

Tyr Ile Lys Gln Ala Ala Leu His Tyr Ala Asn Gln Leu Lys Gln Leu
            260                 265                 270

Gln Ile Asn Thr Ser Gln Met Ser Met Gln Ala Cys Tyr Gly Thr
        275                 280                 285

Gln Asn Leu Gln Ala Ile Asp Leu His Thr Ser Ala Gly Tyr Pro Tyr
    290                 295                 300

Ser Ala Leu Gly Ile Lys Lys Arg Asp Ile Leu Asp Pro Thr Thr Arg
305                 310                 315                 320

Asp Val Ser Arg Met Lys Phe Tyr Met Asp Lys Tyr Gly Leu Asp Leu
                325                 330                 335

Pro Tyr Ser Thr Tyr Val Lys Asp Gln Leu Arg Ser Ile Asp Lys Ile
            340                 345                 350

Lys Lys Gly Lys Ser Arg Leu Ile Gln Ala Ser Ser Leu Asn Asp Ser
        355                 360                 365

Val Tyr Leu Arg Met Ala Phe Gly His Leu Tyr Gln Ala Phe His Ala
    370                 375                 380

Asn Pro Gly Thr Ile Thr Gly Ser Ala Val Gly Cys Asn Pro Asp Thr
385                 390                 395                 400

Phe Trp Ser Lys Leu Pro Ile Leu Leu Pro Gly Ser Leu Phe Ala Phe
                405                 410                 415
```

Asp Tyr Ser Gly Tyr Asp Ala Ser Leu Ser Pro Val Trp Phe Arg Ala
            420                 425                 430

Leu Gln Leu Val Leu Arg Gln Ile Gly Tyr Ser Gln Ala Ile Ser
        435                 440                 445

Leu Ile Gln Gly Ile Asn His Thr His Val Tyr Arg Asn Lys Thr
450                 455                 460

Tyr Cys Val Leu Gly Gly Met Pro Ser Gly Cys Ser Gly Thr Ser Ile
465                 470                 475                 480

Phe Asn Ser Met Ile Asn Asn Ile Ile Ile Arg Ala Leu Leu Ile Lys
                485                 490                 495

Thr Phe Lys Gly Ile Asp Leu Asp Gln Leu Asn Met Val Ala Tyr Gly
            500                 505                 510

Asp Asp Val Leu Ala Ser Tyr Pro Phe Pro Ile Asp Cys Leu Gln Leu
            515                 520                 525

Ala Lys Thr Gly Lys Gln Tyr Gly Leu Thr Met Thr Pro Ala Asp Lys
530                 535                 540

Ser Pro Cys Phe Asn Gln Val Asn Trp Gly Asn Ala Thr Phe Leu Lys
545                 550                 555                 560

Arg Gly Phe Leu Pro Asp Gln Gln Phe Pro Phe Leu Ile His Pro Thr
                565                 570                 575

Met Pro Met Arg Gln Ile His Gln Ser Ile Arg Trp Thr Lys Asp Ala
            580                 585                 590

Arg Asn Thr Gln Asp His Val Arg Ser Leu Cys Leu Leu Ala Trp His
            595                 600                 605

Asn Gly Lys Gln Gln Tyr Gln Lys Phe Val Ser Thr Ile Arg Ser Val
            610                 615                 620

Pro Val Gly Arg Ala Leu Ala Ile Pro Asn Tyr Gln Asn Leu Arg Arg
625                 630                 635                 640

Asn Trp Leu Gln Leu Phe
                645

<210> SEQ ID NO 5
<211> LENGTH: 39
<212> TYPE: DNA
<213> ORGANISM: Artificial Sequence
<220> FEATURE:
<223> OTHER INFORMATION: PCR amplification was performed using a yeast
      genomic DNA as a template and using MOXP-F

<400> SEQUENCE: 5
cgagctcctc gaggcggaga acgatctcct cgagctgct                              39

<210> SEQ ID NO 6
<211> LENGTH: 43
<212> TYPE: DNA
<213> ORGANISM: Artificial Sequence
<220> FEATURE:
<223> OTHER INFORMATION: PCR amplification was performed using a yeast
      genomic DNA as a template and using MOXP-R

<400> SEQUENCE: 6
cttccacgtc tccgaattcc cgggatccgt ttttgtactt tag                         43

<210> SEQ ID NO 7
<211> LENGTH: 41
<212> TYPE: DNA
<213> ORGANISM: Artificial Sequence
<220> FEATURE:
<223> OTHER INFORMATION: PCR amplification was performed using a yeast genomic DNA as a template and using MOXT-F

<400> SEQUENCE: 7
aagtacaaaa acggatcccg cggaattcgg agacgtggaa g     41

<210> SEQ ID NO 8
<211> LENGTH: 38
<212> TYPE: DNA
<213> ORGANISM: Artificial Sequence
<220> FEATURE:
<223> OTHER INFORMATION: PCR amplification was performed using a yeast
      genomic DNA as a template and using MOXT-R

<400> SEQUENCE: 8
gctatggccg acgtcgacct gctcaatctc cggaatgg     38

<210> SEQ ID NO 9
<211> LENGTH: 33
<212> TYPE: DNA
<213> ORGANISM: Artificial Sequence
<220> FEATURE:
<223> OTHER INFORMATION: PCR amplification was performed using a yeast
      genomic DNA as a template and using HARS-F

<400> SEQUENCE: 9
cgagctccag ctgagggcgc tgagccgcaa gtg     33

<210> SEQ ID NO 10
<211> LENGTH: 37
<212> TYPE: DNA
<213> ORGANISM: Artificial Sequence
<220> FEATURE:
<223> OTHER INFORMATION: PCR amplification was performed using a yeast
      genomic DNA as a template and using HARS-R

<400> SEQUENCE: 10
cgtcaaccca attcttatga ccagctgttt gggcgca     37

<210> SEQ ID NO 11
<211> LENGTH: 37
<212> TYPE: DNA
<213> ORGANISM: Artificial Sequence
<220> FEATURE:
<223> OTHER INFORMATION: PCR amplification was performed using a yeast
      genomic DNA as a template and using Ura3-F

<400> SEQUENCE: 11
tgcgcccaaa cagctggtca taagaattgg gttgacg     37

<210> SEQ ID NO 12
<211> LENGTH: 37
<212> TYPE: DNA
<213> ORGANISM: Artificial Sequence
<220> FEATURE:
<223> OTHER INFORMATION: PCR amplification was performed using a yeast
      genomic DNA as a template and using Ura3-R

<400> SEQUENCE: 12
ctaaagggaa gaaaagctgg taaatgaata ttatgtc     37

<210> SEQ ID NO 13
<211> LENGTH: 38
<212> TYPE: DNA
<213> ORGANISM: Artificial Sequence
<220> FEATURE:
<223> OTHER INFORMATION: PCR amplification was performed using a PBR-SK
      plasmid as a template and using primers Amp+ColE1-F

<400> SEQUENCE: 13
tgacataata ttcatttacc agcttttgtt ccctttag                               38

<210> SEQ ID NO 14
<211> LENGTH: 36
<212> TYPE: DNA
<213> ORGANISM: Artificial Sequence
<220> FEATURE:
<223> OTHER INFORMATION: PCR amplification was performed using a PBR-SK
      plasmid as a template and using primers Amp+ColE1-R

<400> SEQUENCE: 14
gctatggccg acgtcgactt aacgcttaca atttag                                 36

<210> SEQ ID NO 15
<211> LENGTH: 24
<212> TYPE: DNA
<213> ORGANISM: Artificial Sequence
<220> FEATURE:
<223> OTHER INFORMATION: Primer sequences of P1 gene for PCR
      amplification

<400> SEQUENCE: 15 agttttttgcc ctacttgatc acag                                             24

<210> SEQ ID NO 16
<211> LENGTH: 31
<212> TYPE: DNA
<213> ORGANISM: Artificial Sequence
<220> FEATURE:
<223> OTHER INFORMATION: Primer sequence of P1 gene for PCR
      amplification

<400> SEQUENCE: 16
cggaattctt attactgggt cacggcctgt c                                      31

<210> SEQ ID NO 17
<211> LENGTH: 27
<212> TYPE: DNA
<213> ORGANISM: Artificial Sequence
<220> FEATURE:
<223> OTHER INFORMATION: Primer sequence of 3CD gene for PCR
      amplification

<400> SEQUENCE: 17
aaccacaccc accacgtgta cagaaac                                           27

<210> SEQ ID NO 18
<211> LENGTH: 25
<212> TYPE: DNA
<213> ORGANISM: Artificial Sequence
<220> FEATURE:
<223> OTHER INFORMATION: Primer sequence of 3CD gene for PCR
      amplification

<400> SEQUENCE: 18
actcgctatt tcagcttttc atctc                                             25

UNITED STATES PATENT AND TRADEMARK OFFICE
CERTIFICATE OF CORRECTION

PATENT NO. : 9,782,471 B2
APPLICATION NO. : 14/891582
DATED : October 10, 2017
INVENTOR(S) : Meirong Gu et al.

It is certified that error appears in the above-identified patent and that said Letters Patent is hereby corrected as shown below:

In the Claims

In Column 37, Claim 9, Line 26, after "A method of preparing a" replace "compostion," with --composition,--.

Signed and Sealed this
Fifth Day of December, 2017

Joseph Matal
*Performing the Functions and Duties of the*
*Under Secretary of Commerce for Intellectual Property and*
*Director of the United States Patent and Trademark Office*